United States Patent [19]
Ghaed et al.

[11] Patent Number: 5,466,416
[45] Date of Patent: Nov. 14, 1995

[54] APPARATUS AND METHODS FOR CARRYING OUT ELECTROCHEMILUMINESCENCE TEST MEASUREMENTS

[76] Inventors: Ali Ghaed, 4605 S. Chelsea La., Bethesda, Md. 20814; Jonathan K. Leland, 14236 Amberleigh Ter., Silver Spring, Md. 20905; Glenn D. Zoski, 10308 Tamarack Dr., Vienna, Va. 22181; Jack E. Goodman, 3011 Third St. North, Arlington, Va. 22201; John T. Grosser, 6 Colony Brook La., Derry, N.H. 03038

[21] Appl. No.: 61,676

[22] Filed: May 14, 1993

[51] Int. Cl.⁶ .......................... G01N 21/76; G01N 21/66
[52] U.S. Cl. .......................... 422/52; 422/81; 422/82.08; 422/82.09; 250/361 C; 250/362; 250/369; 324/71.1; 435/808
[58] Field of Search .......................... 422/52, 81, 82.05, 422/82.08, 82.09; 324/71.1; 436/172; 250/361 C, 362, 369

[56] References Cited

U.S. PATENT DOCUMENTS

| | | | |
|---|---|---|---|
| 5,061,445 | 10/1991 | Zoski et al. | 422/82 |
| 5,068,088 | 11/1991 | Hall et al. | 422/82 |
| 5,093,268 | 3/1992 | Leventis et al. | 436/172 |
| 5,147,806 | 9/1992 | Kamin et al. | 436/149 |
| 5,247,243 | 9/1993 | Hall et al. | 324/71.1 |

FOREIGN PATENT DOCUMENTS

| | | |
|---|---|---|
| WO89/10552 | 11/1989 | WIPO. |
| WO90/05411 | 5/1990 | WIPO. |
| WO90/11511 | 10/1990 | WIPO. |
| WO92/14139 | 8/1992 | WIPO. |
| WO92/14138 | 8/1992 | WIPO. |
| WO93/01308 | 1/1993 | WIPO. |

*Primary Examiner*—David A. Redding

[57] ABSTRACT

An apparatus as provided for use in carrying out electrochemiluminescence test measurements. The apparatus includes a cell to contain an electrochemiluminescence sample fluid. A working electrode is provided within the cell and is coupled to a supply of electrical energy to apply the same to the sample fluid. A temperature effect adjustment system serves either to adjust a temperature of the electrochemiluminescent sample fluid so that it is within a predetermined range, or else adjusts an output signal representing light produced through electrochemiluminescence of the sample fluid based on the temperature of the sample fluid.

10 Claims, 27 Drawing Sheets

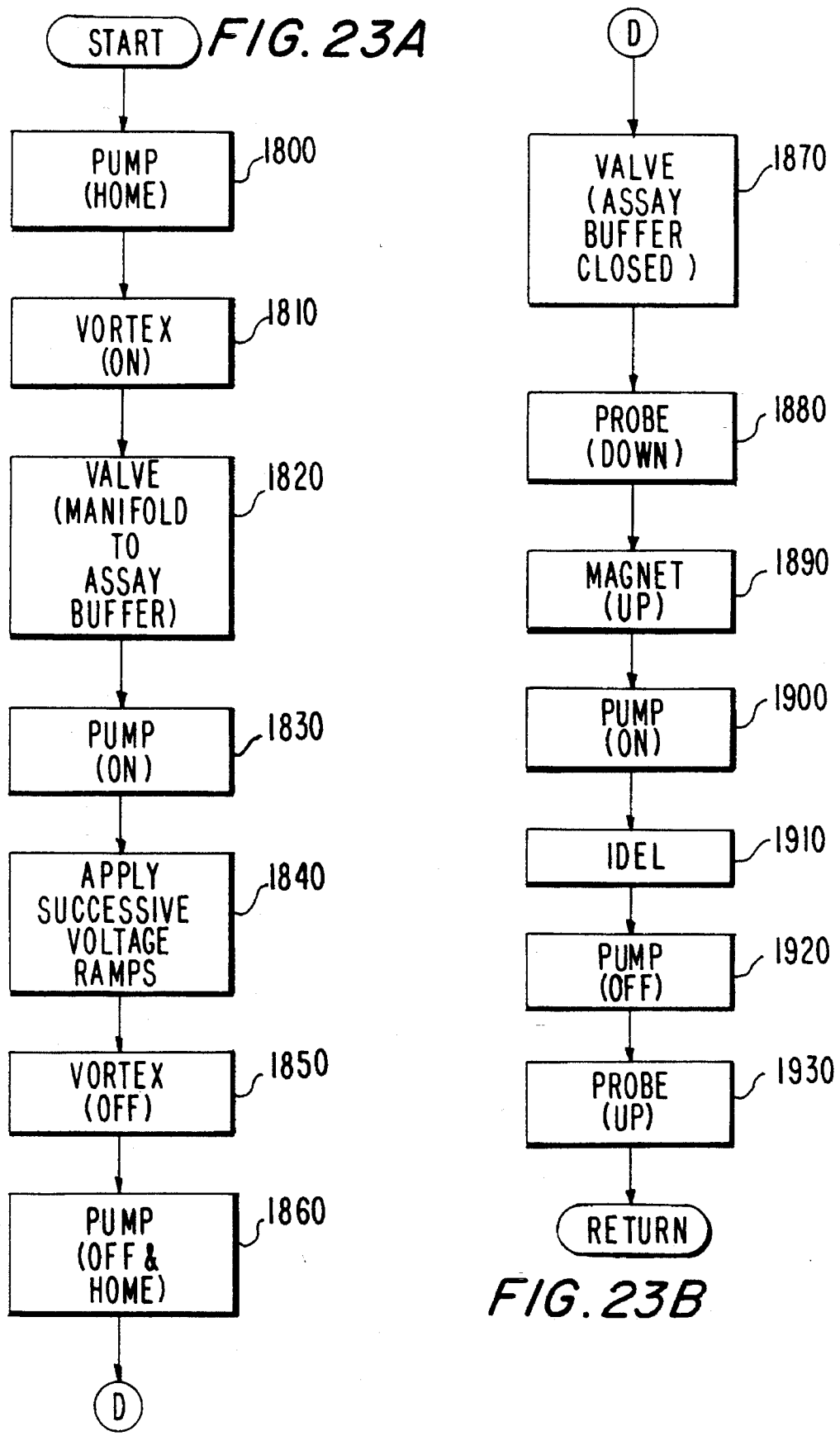

APPARATUS AND METHODS FOR CARRYING OUT ELECTROCHEMILUMINESCENCE TEST MEASUREMENTS

BACKGROUND OF THE INVENTION

This application relates generally to apparatus and methods for detecting the presence of and/or measuring analytes of interest by inducing and detecting electrochemiluminescence in a test sample.

Numerous methods and systems have been developed for the detection and quantitation of analytes of interest in biochemical and biological substances. Methods and systems which are capable of measuring trace amounts of microorganisms, pharmaceuticals, hormones, viruses, antibodies, nucleic acids and other proteins are of substantial value to researchers and clinicians.

Chemiluminescent assay techniques have been adopted in which a sample containing an analyte of interest is mixed with a reactant labeled with chemiluminescent label. The reactive mixture is incubated and some portion of the labeled reactant binds to the analyte. After incubation, the bound and unbound fractions of the mixture are separated and the concentration of the label in either or both fractions can be determined by chemiluminescent techniques. The level of chemiluminescence determined in one or both fractions indicates the amount of the analyte of interest in the sample. Electrochemiluminescent (ECL) assay techniques provide improvements over chemiluminescent techniques. They provide a sensitive and precise measurement of the presence and concentration of an analyte of interest. In ECL techniques the incubated sample is exposed to a voltammetric working electrode in order to trigger luminescence. In the proper chemical environment, such electrochemiluminescence is triggered by a voltage impressed on the working electrode at a particular time and in a particular manner. Light produced by an electrochemiluminescent label is measured to provide an indication of the presence of the analyte or to measure the same.

While ECL techniques have been developed for use in the laboratory, there is a need for a practical ECL instrument capable of carrying out multiple assays in an efficient and reproducible manner.

OBJECTS AND SUMMARY OF THE INVENTION

It is an object of the present invention to provide improved apparatus for carrying out electrochemiluminescence test measurements.

It is another object of the invention to provide such an apparatus which is versatile and easy to use.

It is a further object of the invention to provide an electrochemiluminescence test apparatus which affords reproducible and accurate ECL test results.

It is still another object of the present invention to provide an electrochemiluminescence test apparatus which operates efficiently.

In accordance with the an aspect of the present invention, an apparatus for use in carrying out electrochemiluminescence test measurements comprises: a cell for containing an electrochemiluminescent sample fluid; a working electrode having an electrode surface within the cell; a supply of electrical energy coupled with the working electrode for supplying electrical energy to the electrochemiluminescent sample fluid in the cell; output signal producing means for producing an output signal representing a detected value based on light produced through electrochemiluminescence of the sample fluid within the cell; and a programmable control system coupled with the supply of electrical energy and the output signal producing means for controlling the application of electrical energy to the electrochemiluminescent sample fluid and the production of the output signal in accordance with an assay control program stored in the programmable control system.

In accordance with another aspect of the present invention, a method for carrying out electrochemiluminescent test measurements comprises the steps of introducing a sample fluid to a cell having a working electrode therein; supplying electrical energy to the electrochemiluminescent sample fluid in the cell through the working electrode; producing an output signal representing a detected value based on light produced through electrochemiluminescence of the sample fluid within the cell; and controlling the application of electrical energy to the electrochemiluminescent sample fluid and the production of the output signal in accordance with an assay control program stored in a programmable control system.

In accordance with another aspect of the present invention, an apparatus is provided for use in carrying out electrochemiluminescence test measurements, comprising: a cell for containing an electrochemiluminescent sample fluid; a working electrode having an electrode surface within the cell; a supply of electrical energy coupled with the working electrode for supplying electrical energy to the electrochemiluminescent sample fluid within the cell; output signal producing means for producing an output signal representing a detected value based on light produced through electrochemiluminescence of the sample fluid within the cell; and temperature effect adjustment means for carrying out at least one of adjusting a temperature of the electrochemiluminescent sample fluid to a value at least within a predetermined range of temperature values, and adjusting the output signal based on the temperature of the electrochemiluminescent sample fluid to produce a temperature effect adjusted output signal.

In accordance with a further aspect of the present invention, an apparatus for use in carrying out electrochemiluminescence test measurements comprises: a flow cell housing defining a sample container for holding an electrochemiluminescent fluid sample, the flow cell having a sample fluid inlet for introducing the electrochemiluminescent fluid sample to the sample container and a sample fluid outlet for emitting the sample fluid from the sample container, the fluid inlet, the sample container and the fluid outlet defining a fluid flow path through the flow cell housing; a working electrode and a counter electrode disposed within the sample container for exposure to the electrochemiluminescent fluid sample therein; the flow cell housing defining an ionic medium container coupled with the fluid flow path to permit ionic exchange therebetween; and a reference electrode; the reference electrode being disposed within the ionic medium container for exposure to ionic media therein.

In accordance with still another aspect of the present invention, an apparatus is provided for use in carrying out electrochemiluminescence test measurements, comprising: a fluid container defining a fluid flow path therethrough, the fluid container having a sample fluid inlet for introducing an electrochemiluminescent fluid sample to the fluid flow path and a fluid outlet for emitting the fluid sample from the fluid flow path for conducting fluids through the fluid container along a flow direction through the fluid flow path from the fluid inlet to the fluid outlet; working electrode means for applying electrical energy to the fluid sample adjacent a working electrode surface thereof; the working electrode surface being disposed to one side of the fluid flow path and the fluid container having a light transmissive portion defining a light transmissive wall of the fluid flow path opposite the working electrode for enabling transmission of light therethrough produced by electrochemiluminescence of the sample fluid adjacent the working electrode surface; and counter electrode means for providing an electric current through the sample fluid to the working electrode surface, the counter electrode means including a first portion disposed upstream of the working electrode surface and a second portion disposed downstream of the working electrode surface.

In accordance with a still further aspect of the present invention, an apparatus for use in conducting electrochemiluminescence test measurements comprises: a fluid container defining a fluid flow path therethrough, the fluid container having a fluid inlet for introducing a fluid sample to the fluid flow path and a fluid outlet for emitting the fluid sample from the fluid flow path for conducting fluids through the fluid container along a flow direction through the fluid flow path from the fluid inlet to the fluid outlet; a counter electrode positioned within the fluid container and having an electrode surface exposed to fluids within the fluid flow path; and a working electrode positioned within the fluid container and having an electrode surface exposed to fluids within the fluid flow path; the electrode surface of the working electrode being displaced from the electrode surface of the counter electrode laterally with respect to the flow direction of fluid within the fluid flow path such that conductive material entering fluid within the fluid flow path from the electrode surface of one of the counter electrode and the working electrode is prevented from forming a conductive bridge with the other of the counter electrode and the working electrode.

In accordance with yet still another aspect of the present invention, an apparatus is provided for agitating an electrochemiluminescent test sample in a sample container, the sample container having a mouth for permitting withdrawal of the electrochemiluminescent test sample therefrom and a body extending away from the mouth, comprising: a base; a first member movably mounted with respect to the base and including first means for engaging the body of the sample container at a first position; a second member fixedly mounted with respect to the base and including second means for engaging the body of the sample container at a second position between the first position and the mouth thereof; and first motive means for moving the first member so that at least a portion of the sample container adjacent the first position thereof together with the electrochemiluminescent test sample therein is agitated in response to the motion of the first member.

In accordance with a yet still further aspect of the present invention, an apparatus is provided for use in carrying out electrochemiluminescence test measurements of a test sample in a sample container, comprising: means for agitating the test sample; cell means for containing the test sample; sample transport means for transporting the test sample from the sample container to the cell means; means for applying electrical energy to the sample contained by the cell means to induce electrochemiluminescence by the sample; and output signal producing means for producing an output signal representing light emitted by the sample through electrochemiluminescence.

In accordance with a further aspect of the present invention, a method for carrying out electrochemiluminescence test measurements of a test sample in a sample container comprises the steps of: agitating the test sample; transporting the test sample from the sample container to a test cell; applying electrical energy to the sample contained by the test cell to induce electrochemiluminescence by the sample; and producing an output signal representing light emitted by the sample through electrochemiluminescence.

In accordance with another aspect of the present invention, an apparatus is provided for use in carrying out electrochemiluminescence test measurements comprising: a rotatable support member having a plurality of locations thereon for each supporting a corresponding one of a plurality of fluid containers a least some of which contain electrochemiluminescent fluid samples; an electrochemiluminescence test apparatus; a motor system operatively coupled with the rotatable support member to rotate the same to position each of the plurality of fluid containers at a predetermined sampling position in a predetermined sequence; and a fluid sampling system coupled with the electrochemiluminescence test apparatus for successively transferring electrochemiluminescent test samples from the plurality of fluid containers as each is transported to the predetermined sampling position; the rotatable support member including a first drive member having an outer peripheral surface; the motor system having a second drive member coupled with the outer peripheral surface of the first drive member to drive the first drive member for rotating the rotatable support member.

In accordance with a further aspect of the present invention, an apparatus is provided for use in carrying out electrochemiluminescence test measurements, comprising: a movable support having a plurality of spaced apart support positions for each releasably holding a sample container for an electrochemiluminescent test sample at a predetermined container position; an electrochemiluminescence test apparatus; a motor system operatively coupled with the movable support to move the same to present each of the support positions thereof at a predetermined sample transfer location in a predetermined sequence; a sample transfer device located at the predetermined sample transfer location and operative in response to an actuation signal to transfer an electrochemiluminescent test sample from a sample container present at the predetermined sample transfer location to the electrochemiluminescence test apparatus; and a detection system operative to detect the presence of a sample container at the predetermined sample transfer location and to produce the actuation signal based on the detected presence of the sample container.

In accordance with still another aspect of the present invention, a method is provided for carrying out electrochemiluminescence test measurements comprising the steps of: providing a movable support having a plurality of spaced apart support positions for each releasably holding a sample container for an electrochemiluminescent test sample at a predetermined container position and an electrochemiluminescence test apparatus; moving the movable support to present each of the support positions thereof at a predetermined sample transfer location in a predetermined sequence; detecting the presence of a sample container at the predetermined sample transfer location to produce an actuation signal based on the detected presence of the sample container; and transferring an electrochemiluminescent test sample from a sample container present at the predetermined sample transfer location to the electrochemiluminescence test apparatus in response to the actuation signal.

The above, and other objects, features and advantages of the invention will be apparent in the following detailed description of certain illustrative embodiments thereof which is to be read in connection with the accompanying drawings forming a part hereof, and wherein corresponding parts and components are identified by the same reference numerals in the several views of the drawings.

BRIEF DESCRIPTION OF THE DRAWINGS

FIGS. 23A and 23B together provide a flow chart of a tube sampling sub-routine called by the main loop of FIGS. 21A and 21B;

DETAILED DESCRIPTION OF CERTAIN ADVANTAGEOUS EMBODIMENTS

Figure 1:
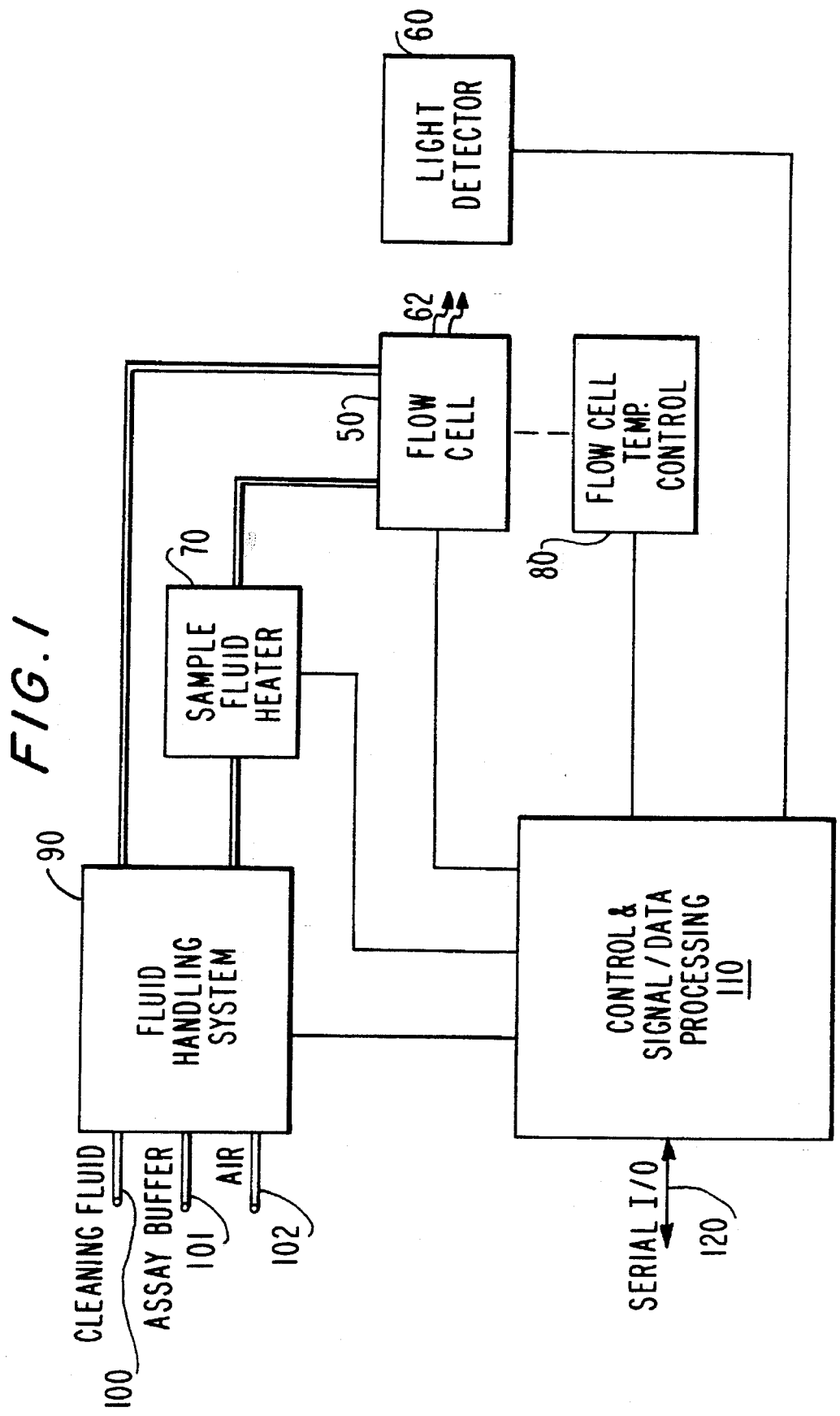
FIG. 1 is a block diagram of an embodiment of an automated electrochemiluminescence test apparatus in accordance with the present invention.

With reference now to the drawings, an apparatus for use in carrying out electrochemiluminescence test measurements in accordance with one embodiment of the present invention is illustrated in FIG. 1 in a generalized block format.

A flow cell 50 serves to apply electrical energy to an electrochemiluminescent fluid sample in a controlled electrochemical environment which is reproducible, in order to induce electrochemiluminescence thereby thus to enable detection and/or quantitation of an analyte to which an ECL label is bound. A light detector 60 is disposed in proximity to the flow cell to receive light 62 emitted by the ECL fluid sample. The light detector 60 produces an electrical signal representing the amount of light received thereby which, after processing, provides a highly accurate measure of the amount of ECL material in the sample. The light detector 60 of the FIG. 1 embodiment advantageously employs a photomultiplier tube to produce the electrical signal, although other detection devices may be employed.

Heretofore, the substantial sensitivity of the electrochemiluminescence process to the temperature of a sample under test, as well as the non-linear character of such temperature dependance, have not been appreciated. In one aspect, the present invention provides temperature effect compensation by carrying out at least one of adjusting a temperature of the electrochemiluminescent fluid sample to a value at least within a predetermined range of temperature values, and adjusting a light output signal representing the light emitted through electrochemiluminescence based on the temperature of the electrochemiluminescent fluid sample to provide a temperature effect adjusted signal. The embodiment of FIG. 1 serves both to adjust the temperature of the electrochemiluminescent fluid sample as well as to adjust measured values of the light based on the actual temperature of the electrochemiluminescent fluid sample in the flow cell 50. Sample fluids supplied to the flow cell 50 (as well as cleaning and conditioning fluids, as explained in greater detail hereinbelow), are subjected to temperature control to at least bring their temperatures to within a predetermined range of temperatures prior to the conduct of the ECL test in the flow cell. For this purpose, both a sample fluid heater system 70 and a flow cell temperature control system 80 are provided.

A fluid handling system 90 serves in general to supply fluids useful for the conduct of ECL tests by the flow cell. Such fluids include cleaning fluids, assay buffers, and air, as well as test sample fluid and calibration sample fluids. The fluid handling system 90 receives cleaning fluids, assay buffers and air through respective inlet conduits 100, 101 and 102, and receives the test and calibration sample fluids from tube containers arranged by a user in a sample holder carousel of the fluid handling system 90, described in greater detail below.

Overall control of the operations carried out by the flow cell 50, the light detector 60, the temperature control systems 70 and 80 and fluid handling system 90, is exercised by a control and signal/data processing system 110 through control lines linking each of these systems and devices therewith. The control and signal/data processing system 110 also receives signals in either or both of analog and digital form over signal lines from each of these systems and devices for processing both to assist in exercising its control functions as well as to input signals for processing to produce test result data to be output by the apparatus via a serial I/O port 120 of the control and signal/data processing system 110. In addition, the control and signal/data processing system 110 is operative to receive programs via the serial I/O port 120 and to store the same for carrying out programmed ECL assays under external control. Typically, such received programs are supplied from a personal computer (PC) in communication with the apparatus via the serial I/O port 120. A user either selects or generates the desired programs with the use of the PC, so that the apparatus of FIG. 1 provides substantial versatility in carrying out ECL tests.

The control and signal/data processing system 110 also carries out temperature compensation of test results based upon temperature data from the flow cell 50, to compensate for any error between the actual sample temperature and a predetermined nominal test temperature.

Figure 2:
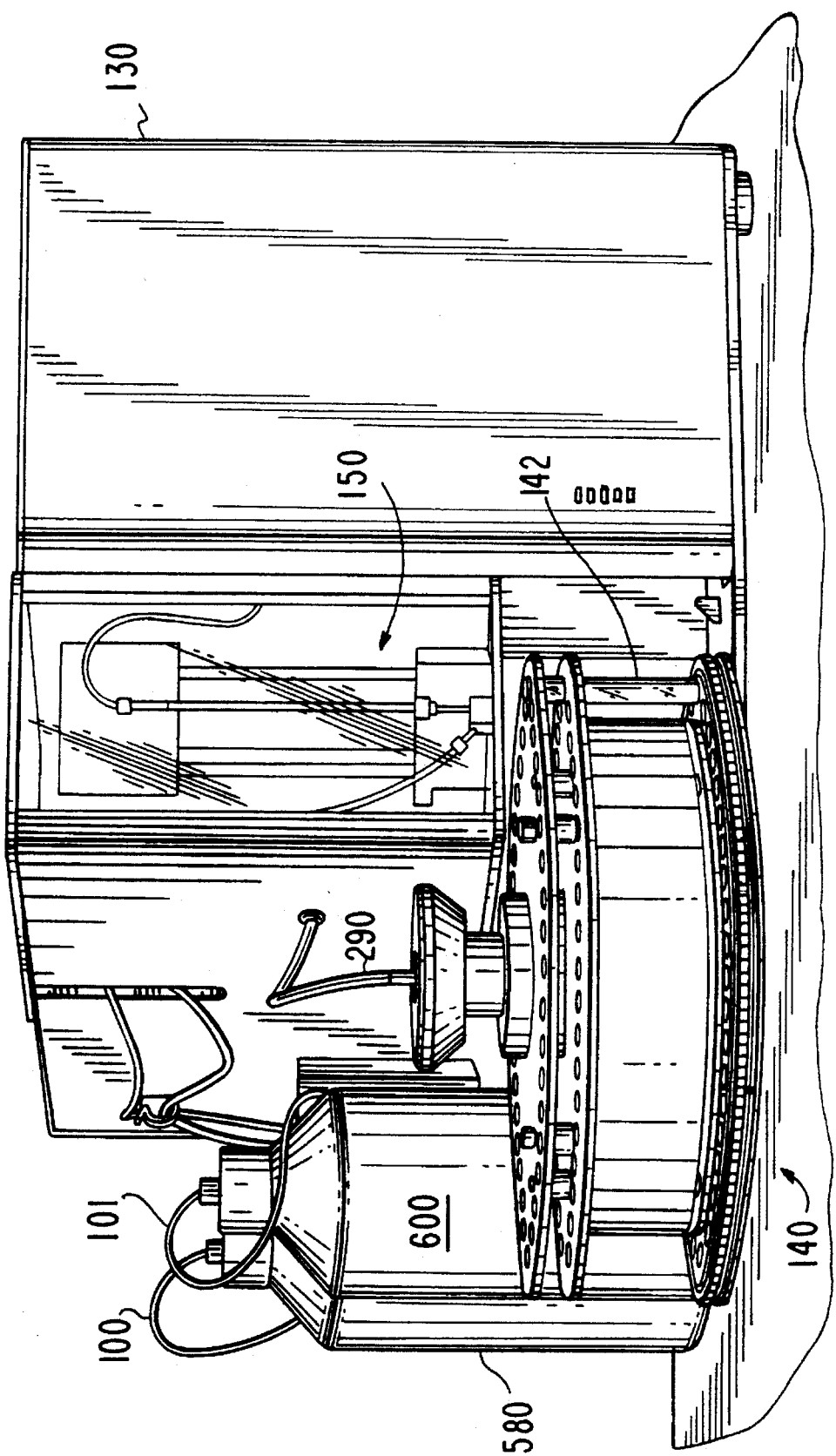
FIG. 2 is a perspective, exterior view of the electrochemiluminescence test apparatus of the FIG. 1 embodiment.

Referring also to FIG. 2, an exterior perspective view of the apparatus of FIG. 1 is there provided wherein certain elements of the fluid handling system 90 of FIG. 1 are visible. As shown in FIG. 2, the apparatus includes an exterior housing 130 in which all of the elements of FIG. 1 embodiment are housed, with the exception of certain components of the fluid handling system 90. As mentioned hereinabove, the fluid handling system 90 includes a sample holder carousel identified in FIG. 2 as 140 which serves to releasably support a plurality of sample fluid and calibration fluid holding tubes 142 each at a respective one of a plurality of horizontally spaced sample holder positions arranged in a circular pattern adjacent a periphery of the sample holder carousel 140. The carousel 140 serves to rotate about a vertical axis in order to present each of the tube holder positions in a predetermined sequence to a predetermined pipetting position at which the fluid contents of a respective holder tube 142 may be aspirated by a pipetting device indicated generally as 150 in FIG. 2 and which is described in greater detail below.

SAMPLE HOLDER CAROUSEL

Figure 3:
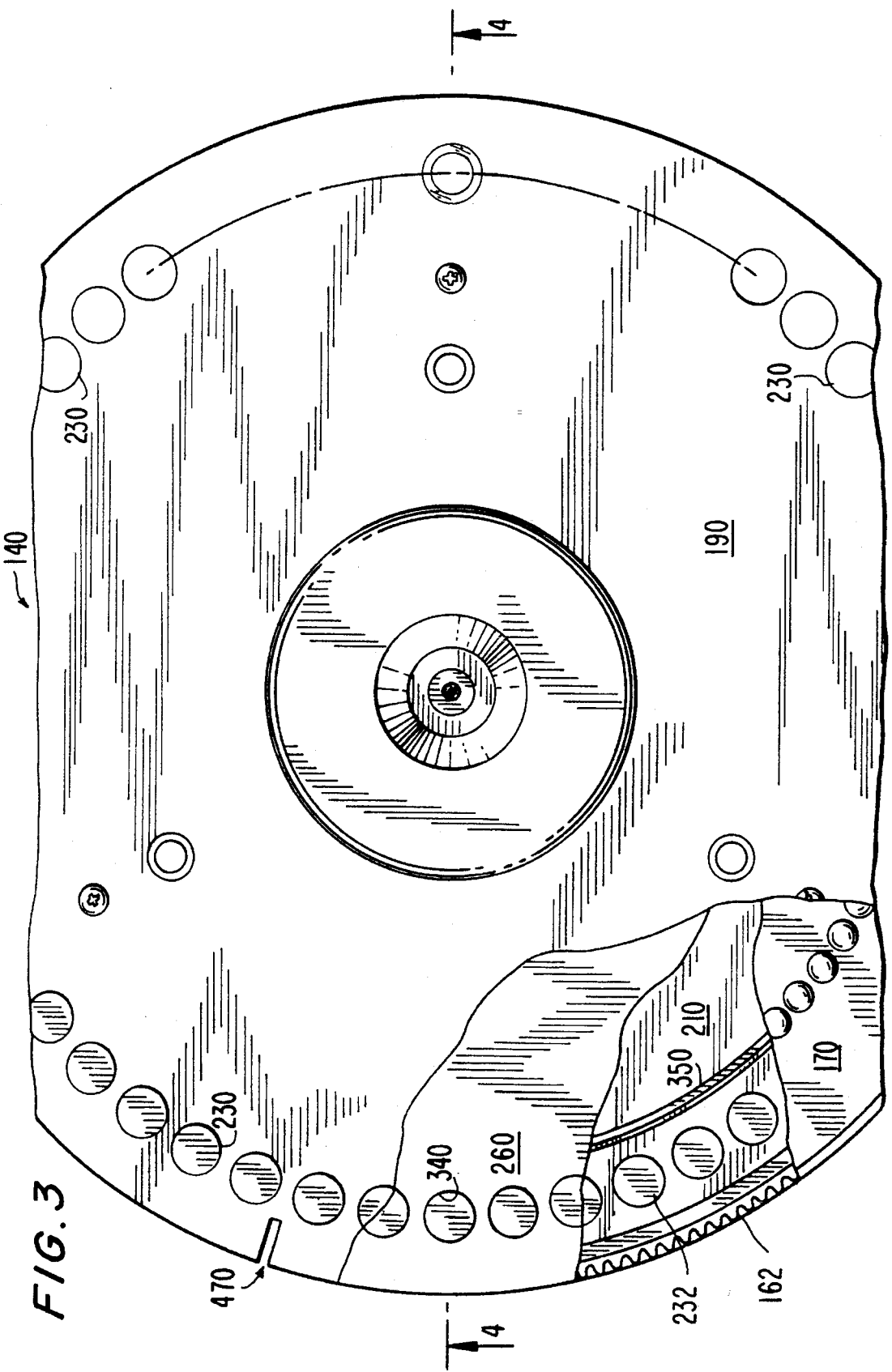
FIG. 3 is a partially broken away, top plan view of a sample holder carousel of the embodiment of FIGS. 1 and 2.
Figure 4:
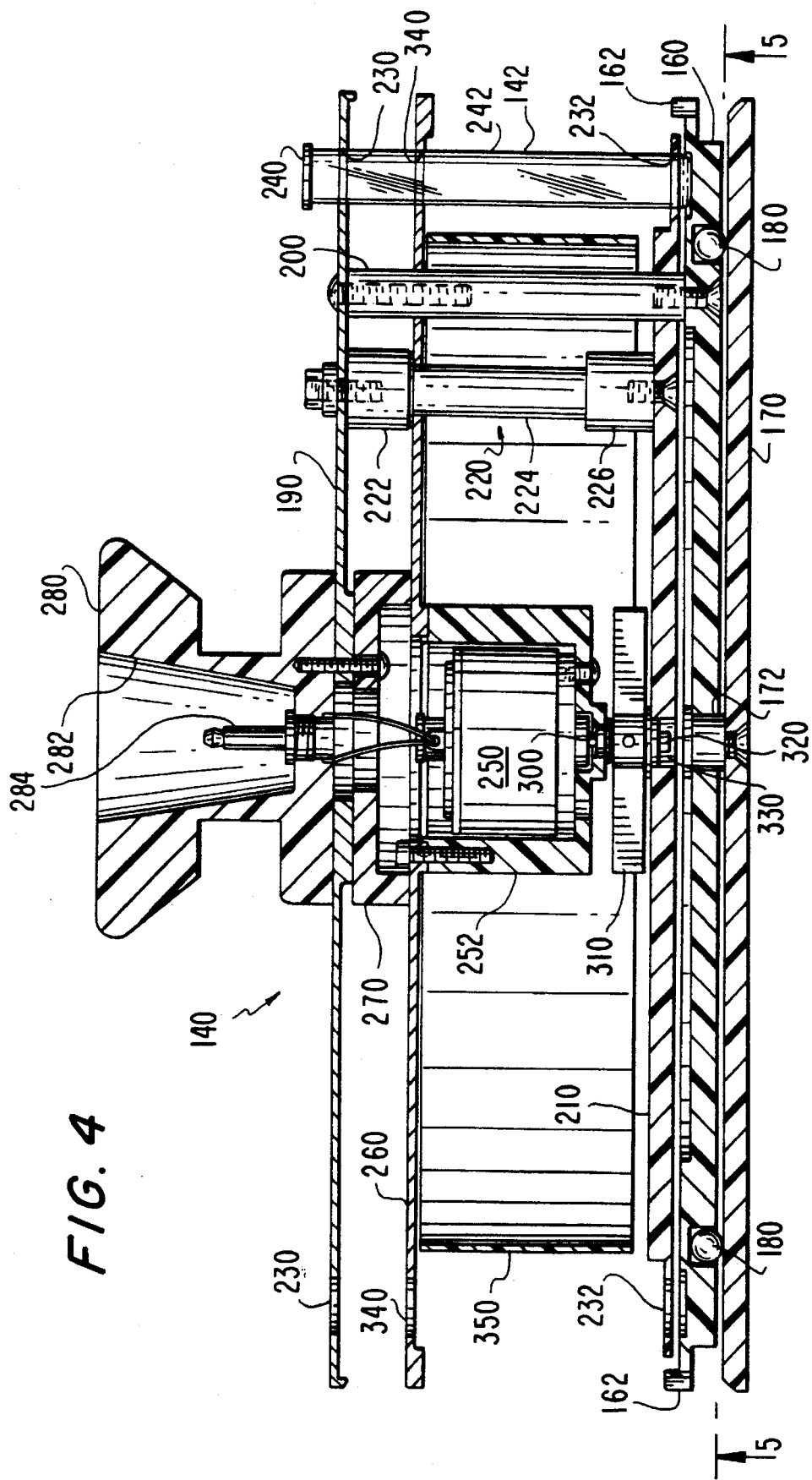
FIG. 4 is a cross-sectional view of the sample holder carousel of FIG. 3 taken along the lines 4—4 therein.
Figure 5:
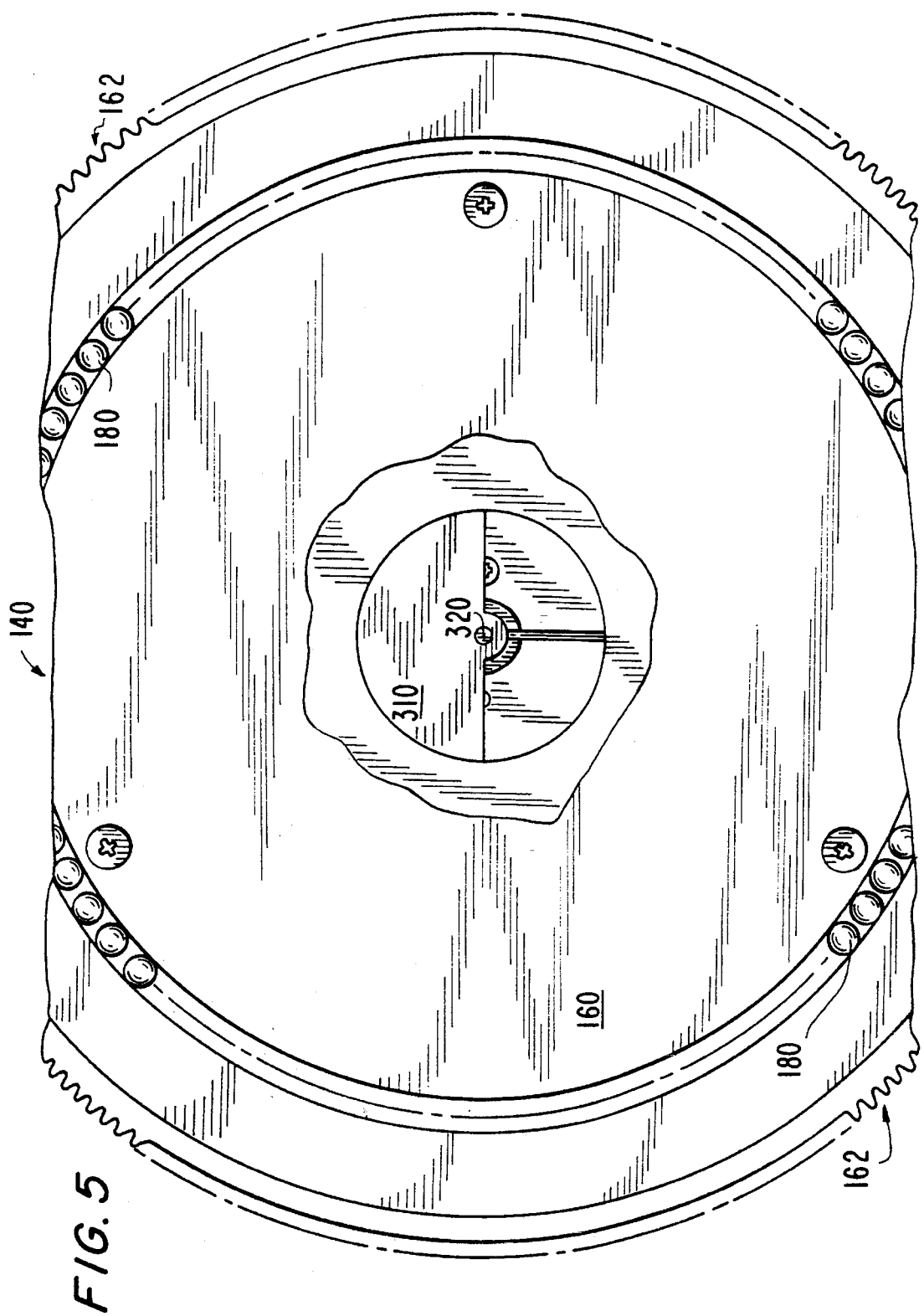
FIG. 5 is a cross-sectional view of the sample holder carousel of FIGS. 3 and 4 taken along the lines 5—5 in FIG. 4.

The sample holder carousel 140 is now described in detail with reference to FIGS. 3–5. The structural relationship of the various elements of the carousel 140 is seen in the cross-sectional view of FIG. 4. As shown in FIG. 4 the carousel 140 includes a rotational base member 160 in a form of a horizontally extending base plate having a generally circular periphery provided with a plurality of gear teeth 162 which may also be seen in FIG. 3. The gear teeth 162 provide a means for rotationally driving the base member 160 together with additional elements of the sample holder carousel 140 mounted thereon, as explained below. The base member 160 is rotationally mounted on a base support member 170 by means of a bearing 172. Lateral rotational support of the base member 160 is provided by a plurality of ball bearings 180 maintained in a race defined by respective grooves in each of the rotational base member 160 and base support member 170.

A first horizontally extending circular plate 190 of the carousel 140 is spaced vertically from and affixed to the rotational base member 160 by a plurality of vertically arranged standoffs 200 affixed by screw fasteners to each of the rotational base member 160 and the first circular plate 190. A second horizontally extending circular plate 210 arranged parallel to and vertically spaced from the rotational base member 160 and the first circular plate 190 is movably coupled with the first circular plate 190 by a plurality of shock mount assemblies 220. Each of the shock mount assemblies includes a first flexible member 222 affixed to the first circular plate 190 by a screw fastener, a vertically arranged cylindrical stand-off 224 affixed to the first flexible member 222 and extending downwardly therefrom, and a second flexible member 226 affixed to the stand-off 224 at a lower extremity thereof and affixed by a screw fastener to the second circular plate 210. The shock mount assemblies 220 permit horizontal movement of the second circular plate 210 with respect to the first circular plate 190 in response to force supplied horizontally to the second circular plate 210, while in the absence of such force, returning the second circular plate 210 to a position generally aligned vertically with the position of the first circular plate 190.

In exemplary ECL assay method, a sample is mixed with a suitable reagent containing an ECL moiety to bind the ECL moiety to the analyte of interest, if present, or to carry out a competitive binding reaction. In certain assays, the result of the reaction is the formation of particulate material to which the ECL moiety is bound. However, this is not an exhaustive explanation of all types of ECL assay methods.

After the binding reaction has taken place, the reacted sample in a holder tube 142 is arranged in a respective holding position in the carousel 140. For this purpose, the first circular plate 190 and the second circular plate 210 are each provided with a plurality of horizontally spaced interior circular walls 230 and 232, respectively arranged in a circular pattern adjacent the outer horizonal periphery of the each of the first and second plates 190 and 210. When the second circular plate 210 is at rest (that is, the absence of the horizontal force applied thereto), each of the interior circular walls 232 of the second circular plate 210 is vertically aligned with a respective one of the interior circular walls 230 of the first circular plate.

As will be seen with reference to FIG. 4, each of the holder tubes 142 includes an upper lip 240 defining a mouth of the holder tube 142 and a body portion 242 extending downwardly from the lip 240 to a lower closed end as shown in the illustration of FIG. 4. The inner circular walls 230 and 232 of the first and second circular plates 190 and 210 are each dimensioned to receive and engage the body 242 of a respective holder tube 142 at respective positions therealong such that the inner wall 230 of the first circular plate 190 engages the body 242 of the holder tube 142 at a position intermediate the mouth defined by the lip 240 and the position at which the inner circular wall 232 of the plate 210 engages the body 242.

After the binding reaction the fluid samples in the sample holder tubes 142 may contain particulate material including the analyze of interest bound to an ECL label. So that a portion of the sample fluid when aspirated by the pipetting device 150 of FIG. 2 will contain a concentration of the particulate material which is representative of the sample overall, it is desired to agitate the sample fluid contained in each of the tubes 142 either prior to or as the sample fluid therein is aspirated by the pipetting device 150. Even where the sample fluid does not contain particulate material, it is desired to agitate the sample fluid either before or during pipetting to ensure a uniform temperature throughout the sample fluid as well as uniform composition thereof.

For this purpose, a motor system is provided in the carousel 140 which serves to apply horizontal force to the second plate 210 so that the same moves horizontally to agitate the lower portion of each of the sample tubes 142 as each is engaged adjacent a lower extremity thereof by a respective inner circular wall 232 of the plate 210 so that the same moves therewith. It will be appreciated that, since the body 242 of the tube 142 is engaged adjacent the lip 240 by the first circular plate which remains stationary with respect to the rotational base member 160, the lip 240 remains substantially in a stationary position as the lower portion of the body 242 is thus agitated. Accordingly, it is possible to reliably introduce the pipetting device 150 into the tube 142 and withdraw a portion of the fluid sample as the tube is agitated. Moreover, since only a portion of the carousel 140 is subjected to agitation (principally the second circular plate 210), this function of the apparatus is relatively efficiently carried out.

The force for moving the lower circular plate 210 is provided by a motor 250 held in a motor housing including a lower member 252 affixed by a screw fastener to a third circular plate 260 which, in turn, is affixed to an upper member 270 of the motor housing. The first circular plate 190 and an upwardly extending handle 280 are both affixed to the upper member 270 by a screw fastener. The handle 280 is provided with an inner wall 282 of generally frusto-conical shape at a bottom surface of which an electrical connector 284 is fastened and coupled electrically with the motor 250 for providing power thereto.

As shown in FIG. 2, the plug 284 is connected with a power cord 290 coupled with a source of power of the apparatus within the exterior housing 130 to controllably energize the motor 250. The configuration of the plug 284 permits the plug 284 to rotate with respect to the cord 290. The motor 250 has a motor shaft 300 coupled with a half-round counterweight 310. With reference also to FIG. 5 the shaft 300 is also coupled with a second shaft 320 having a shaft axis offset from a shaft axis of the motor shaft 300 and journaled for rotation in a bearing 330 affixed to the second circular plate 210. Accordingly, as the shaft of the motor 250 rotates, the offset shaft 320 will likewise rotate while describing a circular translatory motion about the axis of the motor shaft 300. Since the offset shaft 320 is journaled for rotation in the bearing 320 affixed to the second plate 210, the second plate 210 will move with the axis of the offset shaft 320 so that the plate 210 likewise moves with respect to the first plate 190 against force exerted by the shock mount assemblies 220 tending to return the second plate 210 to its rest position with respect to the first plate 190. Consequently, the lower portion of each of the holder tubes 140 which are engaged by the inner circular walls 232 of the second plate 210 will likewise move with the plate 210 in order to agitate the fluid contents of each of the tubes 142. The half-round counterweight 310 balances the system to avoid excessive vibration thereof.

The third circular plate 260 is provided with a plurality of inner circular walls 340 each of which is aligned with a respective one of the inner circular walls 230 of the first circular plate 190 and is dimensioned to receive the body of a respective one of the tubes 142. The carousel 140 also includes a cylindrical wall 350 which extends entirely about the lower member 252 of the motor housing and is spaced relatively close to the positions of the holder tubes 142 to the interior thereof. An outer surface of the cylindrical wall 350 has a flat black finish to provide desired optical properties as explained hereinbelow.

Figure 6:
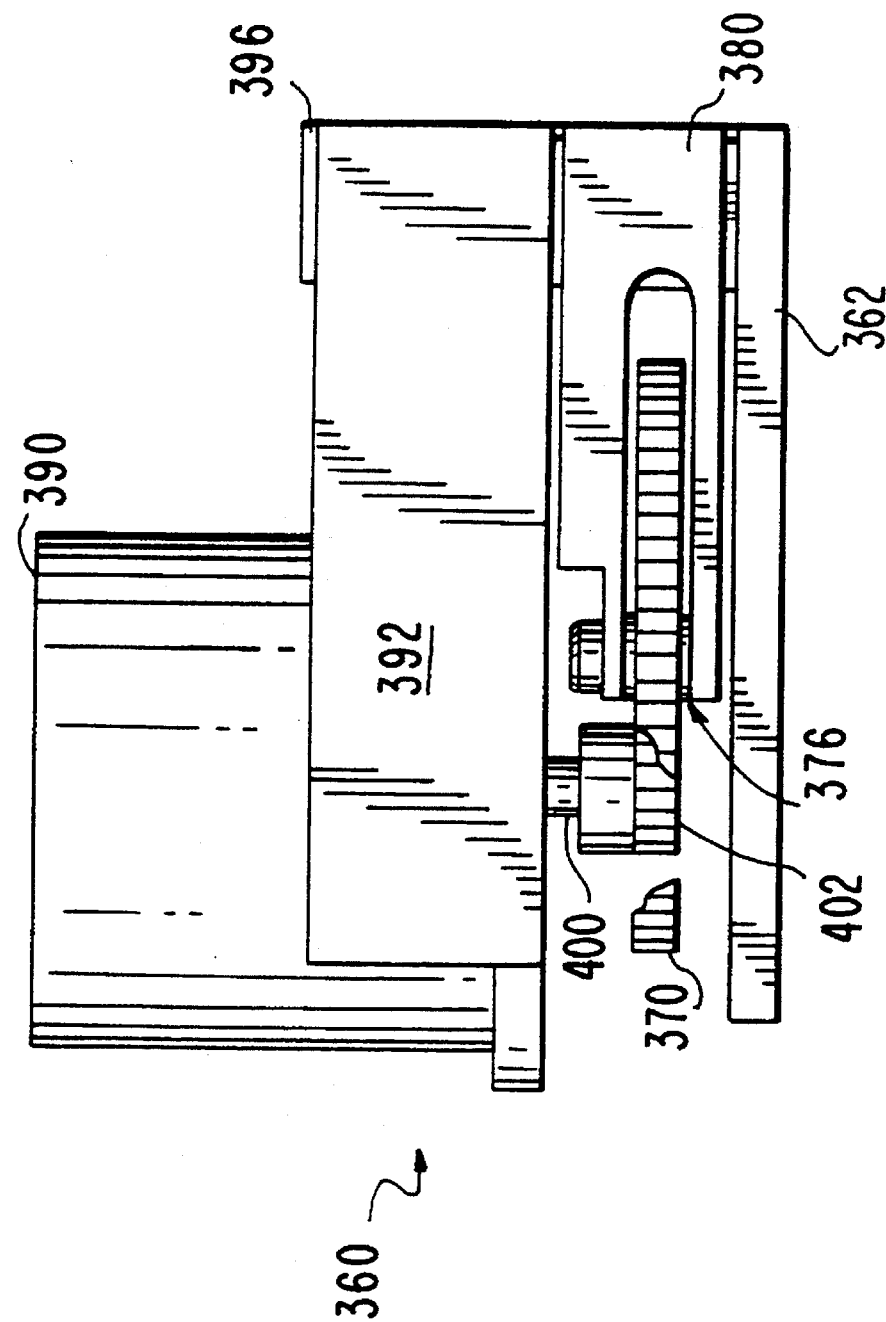
FIG. 6 is a side elevational view of a motor system for rotationally driving the sample holder carousel of FIGS. 3–5.

FIG. 6 illustrates a motor assembly 360 which serves to rotationally drive the rotational base member 160 of the carousel 140, the motor assembly 360 being mounted to a base plate 362 which is independent of the carousel 140. That is, the carousel 140 is supported by its base member 170 independently of the base plate 362.

The motor assembly 360 also includes a gear 370, shown partially broken away, rotatably mounted on a bearing 376 mounted on a idler arm 380 which, in turn, is mounted on the base plate 362. When the carousel 140 is brought into position adjacent the apparatus of FIG. 1, the teeth of gear 370 mesh with the gear teeth 162 of the rotational base member 160 of the carousel 140.

The motor assembly 360 also includes a motor 390 mounted on a motor arm 392 which, in turn, is rotationally mounted on a shaft 396. The motor 390 has a rotational shaft 400 on which a motor gear 402 is mounted. The motor arm 392 is biased by a spring (not shown for purpose of simplicity and clarity) to bring the motor gear 402 into mesh with the gear 370. In other embodiments, the gear 370 and the gear teeth 162 of the base member 160 (FIGS. 4 and 5) may be replaced by a suitable belt drive or frictional drive.

Figure 7:
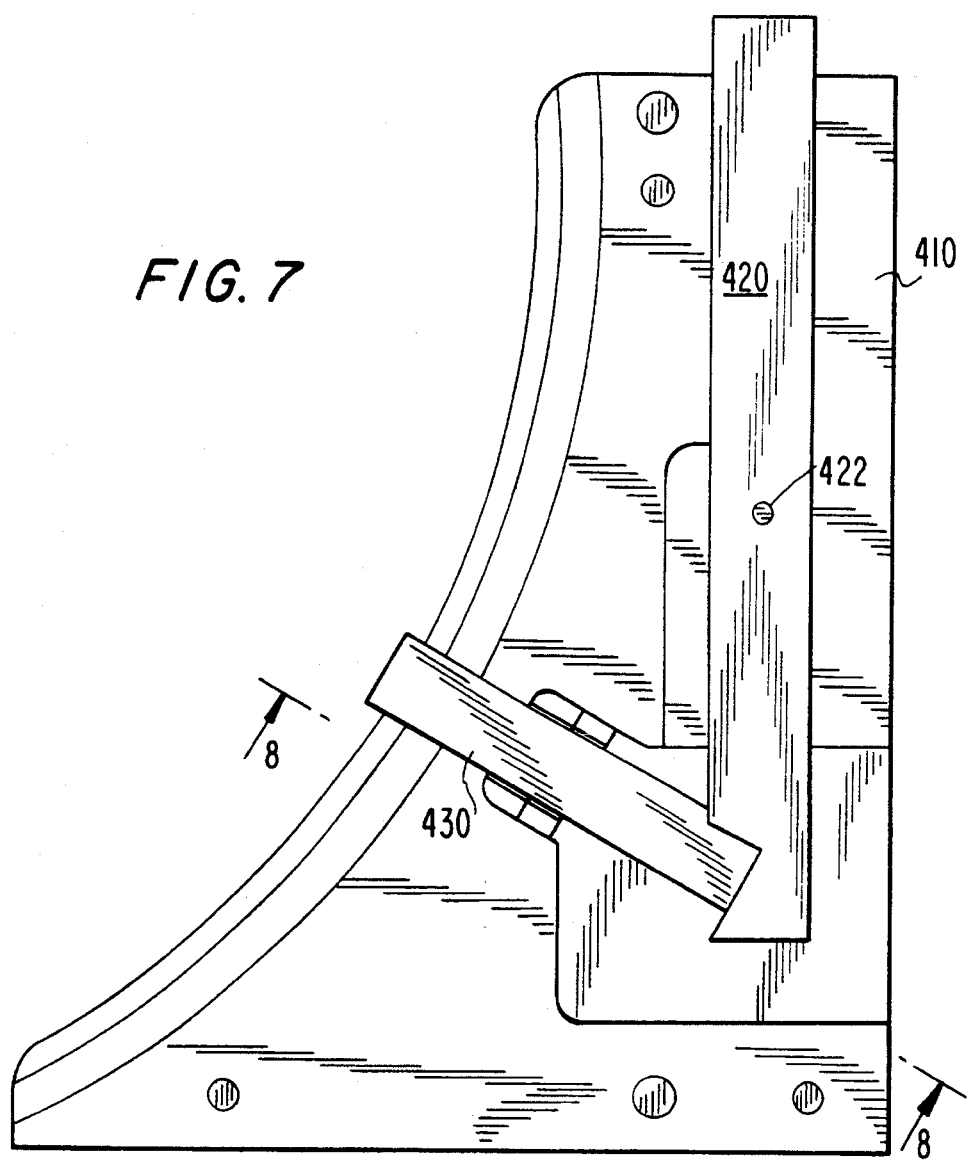
FIG. 7 is a top plan view of a mechanism for releasably securing the sample holder carousel of FIGS. 3–5 against rotation.
Figure 8:
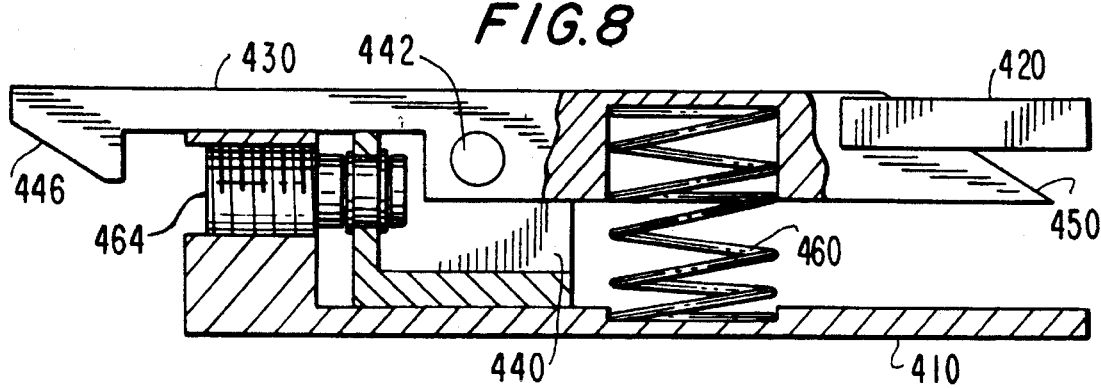
FIG. 8 is a cross-sectional view taken along the lines 8—8 in FIG. 7.

Referring now to FIGS. 7 and 8, a mechanism as illustrated therein for releasably retaining the rotational base member 160, and therefore the holder tubes carried thereby, against rotational movement while fluids are aspirated from the tubes by the pipetting device 150. The holder mechanism includes a base plate 410 on which a lever 420 is mounted for rotation in a horizontal plane about a pivot 422. A latch 430 is pivotally mounted on a slidable carrier 440 for rotation about a pivot 442 in a vertical plane. The latch 430 has a latching end 446 opposite a second end thereof on which cam surface 450 is formed. The lever 420 has a corresponding cam surface which engages the cam surface 450 of the lever 420 so that when the lever 420 is rotated toward the latching end 446 of the latch 430, the latching end 446 is raised to release the rotational base member 160 of the carousel 140, thus to permit rotation thereof. The latching end 446 of the latch 430 is urged downwardly by a coil spring 460 positioned between the base plate 410 and a portion of the latch 430 on a side of the pivot 422 opposite the latching end 446. Consequently, when the lever 420 is rotated away from the latch 430, the latching end 446 thereof is forced downwardly by the coil spring 460 to engage and retain the rotational base member 160 of the sample holder carousel to prevent rotation thereof. The position of the slidable carrier 440, and thus the position of the latch 430 with respect to the base plate 410 is adjustable by means of a set screw 464. The rotation of the lever 420 is actuated by a linear actuator (not shown for purpose of simplicity and clarity) under the control of the system 110 as appropriate to either maintain the carousel in a stationary state or permit it to rotate to present a new tube holder position to the pipetting device 150.

TUBE PRESENCE DETECTOR

Figure 9:
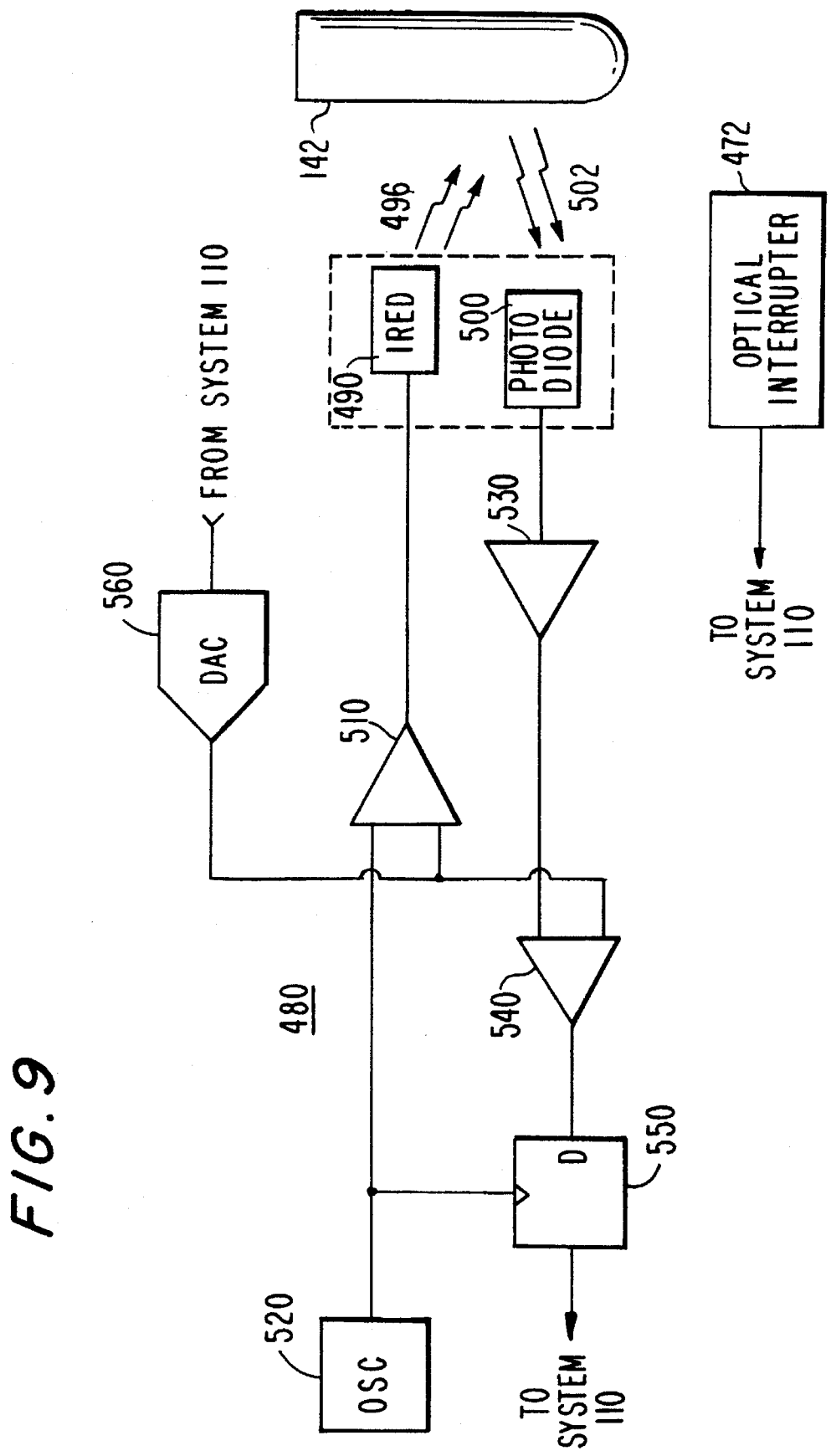
FIG. 9 is a block diagram of a sample tube detector system for detecting the presence of a sample tube in a predetermined sample tube support position of the carousel of FIGS. 3–5.

Referring again to FIG. 3, in order to determine the rotational position of the carousel 140, a homing notch 470 is formed in the first circular plate 190 at a predetermined rotational position thereof. Referring also to FIG. 9, the apparatus is provided with an optical interrupter 472 which produces an output signal indicating to the system 110 of FIG. 1 when the homing notch 470 has been brought into alignment therewith. At that point, the apparatus has determined the absolute rotational position of the carousel 140.

Thereafter, the motor 390, which preferably is a stepper motor, is actuated to rotate the carousel 140 by a predetermined rotational amount to bring a first holder tube position of the carousel 140 into alignment with the pipetting device 150.

Since, depending on the assay being conducted, it is uncertain that a sample holder tube 142 will be present at each of the holder tube positions of the carousel 140, when the carousel is rotated to each holder tube position in succession at the pipetting position, it is necessary to determine whether a holder tube 142 is then present at the pipetting position. In order to make this determination, the apparatus includes a tube presence detector system 480 as illustrated in FIG. 9. The detector system 480 detects the presence of a tube 142 at the pipetting position through the detection of light reflected therefrom. This avoids the need to employ mechanical devices, such as switches, for this purpose, thus avoiding the disadvantage of mechanical wear and the eventual need to replace such devices.

More particularly, the tube presence detector system 480 includes an infra-red emitting diode (IRED) 490 positioned adjacent the pipetting device 150 to project light 496 toward any tube 142 which may be present at the pipetting position. The system 480 also includes a photodiode 500 vertically aligned with the IRED 490 and disposed to receive light 502 reflected from any tube 142 at that position.

The IRED 490 is driven to emit the light 496 in a pulsed fashion in response to a pulsed drive current supplied by a voltage controlled current amplifier 510. An oscillator 520 produces a corresponding pulsed output signal having a 5% duty cycle and a period of 1.6 milliseconds. Accordingly, the voltage controlled current amplifier produces the driving current supplied thereby to the IRED 490 which likewise has a 5% duty cycle and 1.6 millisecond period. By limiting the duty cycle of the current pulse produced by the amplifier 510 to substantially 5% (or such lesser amount as may be practical), the IRED can be driven at a high current level to emit light pulses of relatively high intensity thus to assist in enabling the system 480 to distinguish reflected pulses from background light levels. In addition, since the wall 350 (FIG. 4) has a flat black finish, in the absence of a tube 142 at the pipetting position of the carousel 140, only a relatively small amount of the light will be reflected back towards the photodiode 500 from the wall 350.

An output of the photodiode 500 is coupled with the input of a preamplifier 530 having a band pass characteristic centered on the frequency of the pulses produced by the oscillator 520, which thus serves to assist in rejecting both DC outputs from the photodiode as well as 60 and 120 Hz components from ambient lighting in order to reduce stray light sensitivity of the system 480. An output of the preamplifier 530 is coupled with a first input of a comparator 540 having a second input supplied with a selectable threshold level, as described in greater detail hereinbelow and providing a binary level output. The selectable threshold level is chosen so that, in the absence of a tube 142 at the pipetting position, the signal output by the preamplifier 530 will result in a first state of the output from the comparator 540, while when a tube 142 is present at the pipetting position, the comparator 540 outputs a pulsed binary level signal having the same frequency and duty cycle as the output of the preamplifier 530. The output of the comparator 540 is supplied to the D input of a D-type flip-flop 550 which has a clock input terminal coupled with the output of the oscillator 520. Accordingly, the flip-flop 550 is caused to latch the output of the comparator 540 at the end of the IRED 490 drive on-state thus to synchronize sampling of the signal produced by the light-receiving portion of the system 480 with the pulsed light output by the transmitting portion thereof. The output of the flip-flop 550 is supplied to the control and signal/data processing system 110 thus to provide the system 110 with the ability to determine whether a tube is present at the pipetting position so that the pipetting device 150 may be actuated to aspirate a sample therefrom as appropriate.

The system 110 supplies the selectable threshold level in digital form to the input of a digital-to-analog converter 560 which latches this value and outputs the same in analog form both to the second input of the comparator 540 as well as to a voltage controlled gain input terminal of the voltage controlled current amplifier 510. The foregoing arrangement permits the system 110 to control the sensitivity of the tube presence detector system 480 through a relatively wide dynamic operating range. That is, since both the gain of the amplifier 510 as well as the threshold level of the comparator 540 are controlled by the same signal supplied by the DAC 560, the sensitivity of the system is proportional to the square of the DAC output so that the system's dynamic range is extended as compared with the dynamic range of the DAC 560 output.

By providing the system 110 with the ability to control the sensitivity of the system 480, it is possible for the system 480 to be adjusted to reliably detect the presence of the tubes 142 even though tubes of different colors and materials may be employed which may reflect different amounts of light and even though variations in the positions and dispositions of the tubes 142 may be encountered. In addition, by adjusting the sensitivity of the system 480 by means of a digital output from the system 110, the system 480 is easily calibrated to compensate for IRED's 490 and photodiodes 500 having different characteristics, as well as to compensate for the effects of aging in these components.

Following is a description of an exemplary calibration technique of the system 480. In accordance with the technique, tubes 142 are placed in a number of specified positions in the carousel 140 and the carousel is advanced both to positions where tubes are known to be present as well as positions where it is known that no tubes are present. At each such position, the system 110 supplies a digital ramp signal to the DAC 560 and stores the value thereof at which the flip-flop 550 toggles, this value being referred to as a "calibration threshold". A detection threshold for use in detecting the presence of a tube 142 in normal operation is derived by taking the average of the two calibration thresholds constituting (1) the lowest calibration threshold obtained for the positions at which a tube is present, and (2) the highest calibration threshold obtained for the positions in which a tube is not present. Subsequently, in normal operation the system 110 writes the detection threshold into the DAC 560 for use by the system 480 for detecting tube presence in normal operation.

FLUID HANDLING SYSTEM

Figure 10:
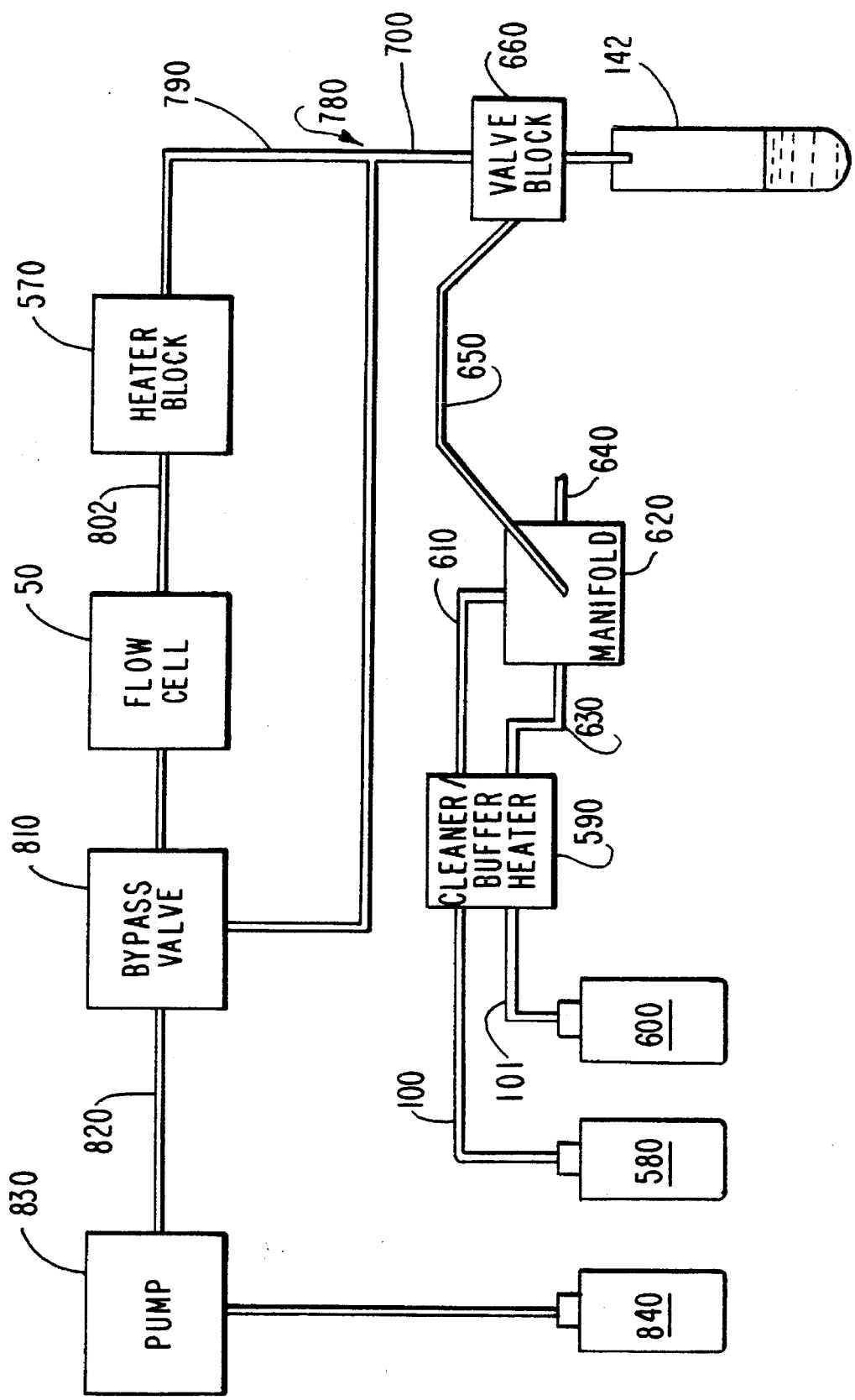
FIG. 10 is a schematic diagram of a fluid handling system of the FIG. 1 embodiment functionally connected with a sample fluid heater system and flow cell thereof for supplying fluids thereto and removing fluids therefrom.

With reference now to FIG. 10, the fluid handling system 90 of FIG. 1 is illustrated in greater detail therein in combination with the flow cell 50 and a heater block 570 of the sample fluid heater 70 of FIG. 1. As shown in FIG. 10, a closed container 580 containing a cleaning fluid is coupled by the line 100 of the fluid handling system 90 to a further heater system 590, while a further closed container 600 containing assay buffer is coupled by the inlet line 101 to the heater system 590. The heater system 590 serves to raise the temperatures of the cleaning fluid and assay buffer supplied from the containers 580 and 600 to within a predetermined temperature range in order to assist in maintaining a desired temperature of the flow cell 50 as well as the remainder of the fluid handling system 90 preceding the flow cell 50 to assist in achieving temperature control of sample fluids subjected ECL tests in the flow cell 50. The operation of the heater systems 70 and 590 will be explaining hereinbelow in greater detail.

After controlled heating by the system 590, the cleaning fluid is supplied via a line 610 to a first inlet of a manifold valve 620, while a further line 630 conducts the assay buffer to a second inlet of the manifold valve 620. A third line 640 open to the air is connected with a third inlet of the manifold valve 620. The manifold valve 620 is solenoid actuated and is operative in response to control signals received thereby to select one of the cleaning fluid, assay buffer and air to be supplied to an outlet thereof coupled with a manifold outlet line 650.

Figure 11:
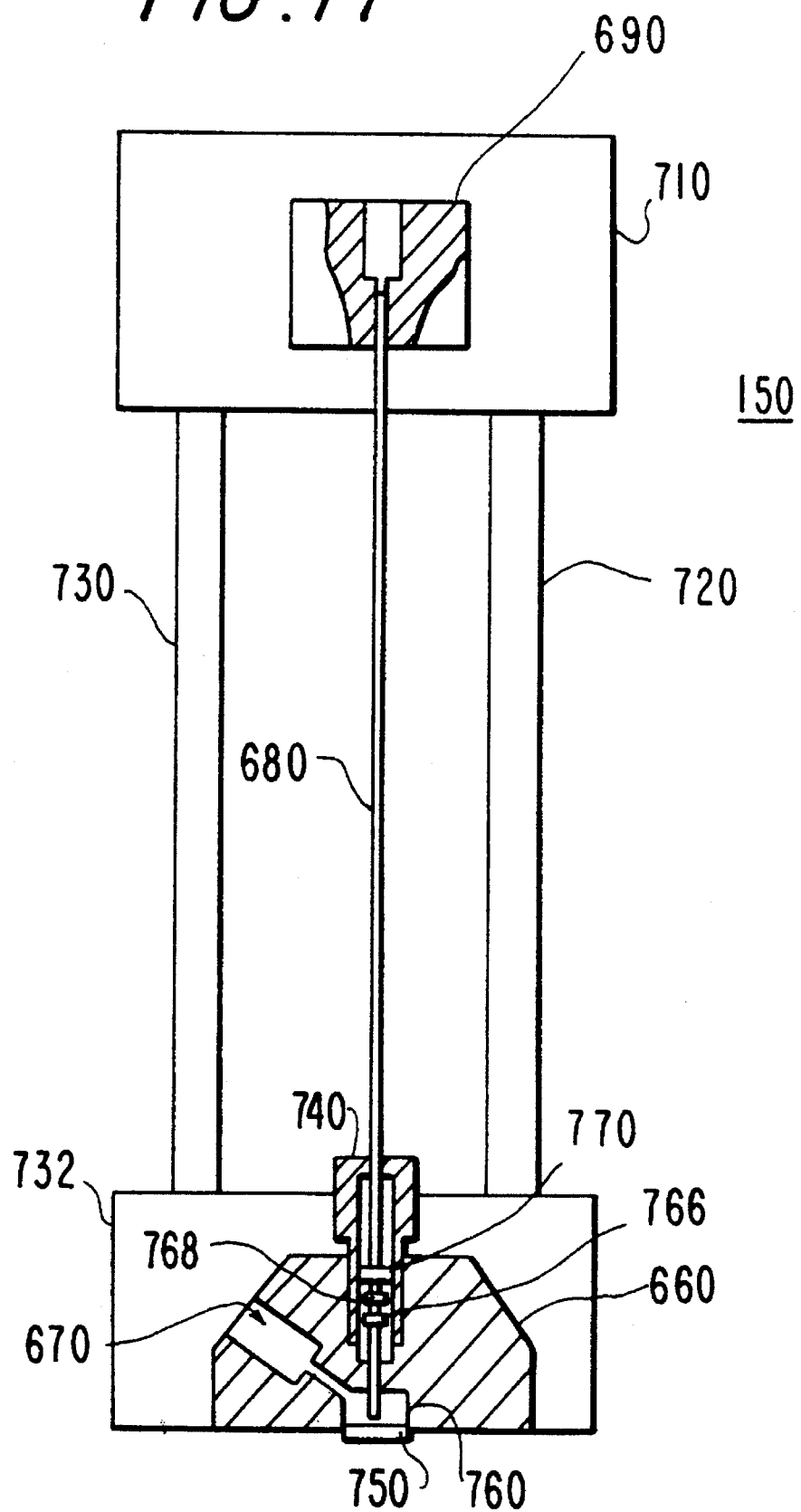
FIG. 11 is a partially cross-sectional, elevational view of a sample pipetting device in combination with a valve block forming a part of the fluid handling system of FIG. 10.

With reference also to FIG. 11, certain elements of the pipetting device 150 are illustrated therein. The pipetting device includes a valve block 660 shown in FIG. 10 and illustrated in cross-section in FIG. 11. An inlet 670 of the valve block 660 is coupled with the manifold outlet line 650 to receive the fluid supplied by the manifold valve 620. The pipetting device 150 includes a probe 680 slidably mounted with respect to the valve block 660 so that the same may be lowered into a respective holder tube 142 to remove liquid therefrom or, in the alternative, raised to a retracted position as shown in FIG. 11. The probe 680 is affixed to a coupling 690 shown in partial cross-section as having a fitting to receive a pipetting device outlet line 700 (FIG. 10). The coupling 690 is mounted on a slidable block 710 slidably mounted on a shaft 720 acting as a linear bearing to guide the block 710 and attached probe 680 as the same is raised and lowered. The block 710 is fitted with a threaded aperture (not shown for purposes of simplicity and clarity) mated with the threads of a lead screw 730. The lead screw 730 is rotatably coupled with a stepper motor (not shown for purposes of simplicity and clarity) which is controllably operable to rotate the lead screw 730 in either of two selectable directions to controllably raise or lower the block 710 and the attached pipetting probe 680. The lead screw 730 and shaft 720 are supported by a base 732.

The pipetting probe 680 is slidably received in a fitting 740 mated with the value block 660 to provide a fluid tight seal therebetween. When the slidable block 710 is fully retracted to its uppermost position as shown in FIG. 11, a poppet mechanism (not shown for purposes of simplicity and clarity) coupled with a spring mounted seal 750 engages the seal 750 in a lower opening 760 of the valve block 660 to form a fluid tight seal therewith. In the disposition as shown in FIG. 11, fluids may be conveyed via the manifold outlet line through the valve block inlet 670 to the probe 680 in order to convey cleaning fluid, assay buffer and/or air to the portion of the fluid handling system 90 downstream of the valve block 660 through the outlet line 700. In addition, cleaning fluid admitted to the valve block through the inlet 670 serves to clean the lower portion of the probe 680.

When the slidable block 710 is lowered by appropriately rotating the lead screw 730, the poppet mechanism is actuated to withdraw the seal 750 from the lower opening 760 to permit the probe 680 to descend from the valve block 660 into a respective one of the holder tubes 142 to aspirate fluid therefrom. When this occurs, a pair of O-ring seals 766 and 768 are forced against a shoulder of the valve block 660 by a washer 770 affixed to the probe 680 to form a fluid tight seal therewith.

The outlet line 700 is coupled with a T-junction 780 having a first outlet coupled with a line 790 through which fluids are conveyed to the heater block 570 of the sample fluid heater system 70 (FIG. 1) to be heated thereby in order to bring the fluids conveyed via the line 790 substantially to a predetermined temperature for the conduct of an ECL measurement by the flow cell 50 which receives the heated fluid from an outlet line 802 of the heater block 570. Fluid received at an inlet of the flow cell 50 from the outlet line 802 is ultimately conveyed via an outlet thereof to a first inlet of a bypass valve 810, a second inlet of the bypass valve 810 being coupled with a second outlet of the T-junction 780. The bypass valve 810 is a solenoid valve operative to couple either the outlet of the flow cell 50 or the second outlet of the T-junction 780 to an outlet line 820 of the bypass valve 810. The outlet line 820 is coupled with an inlet of a peristaltic pump 830 which serves to controllably draw fluids through the fluid handling system 90, heater block 570 and flow cell 50. An outlet of the peristaltic pump 830 is coupled with a waste fluid container 840 for disposal of used fluids.

FLOW CELL HOUSING AND TEMPERATURE CONTROL

Figure 12:
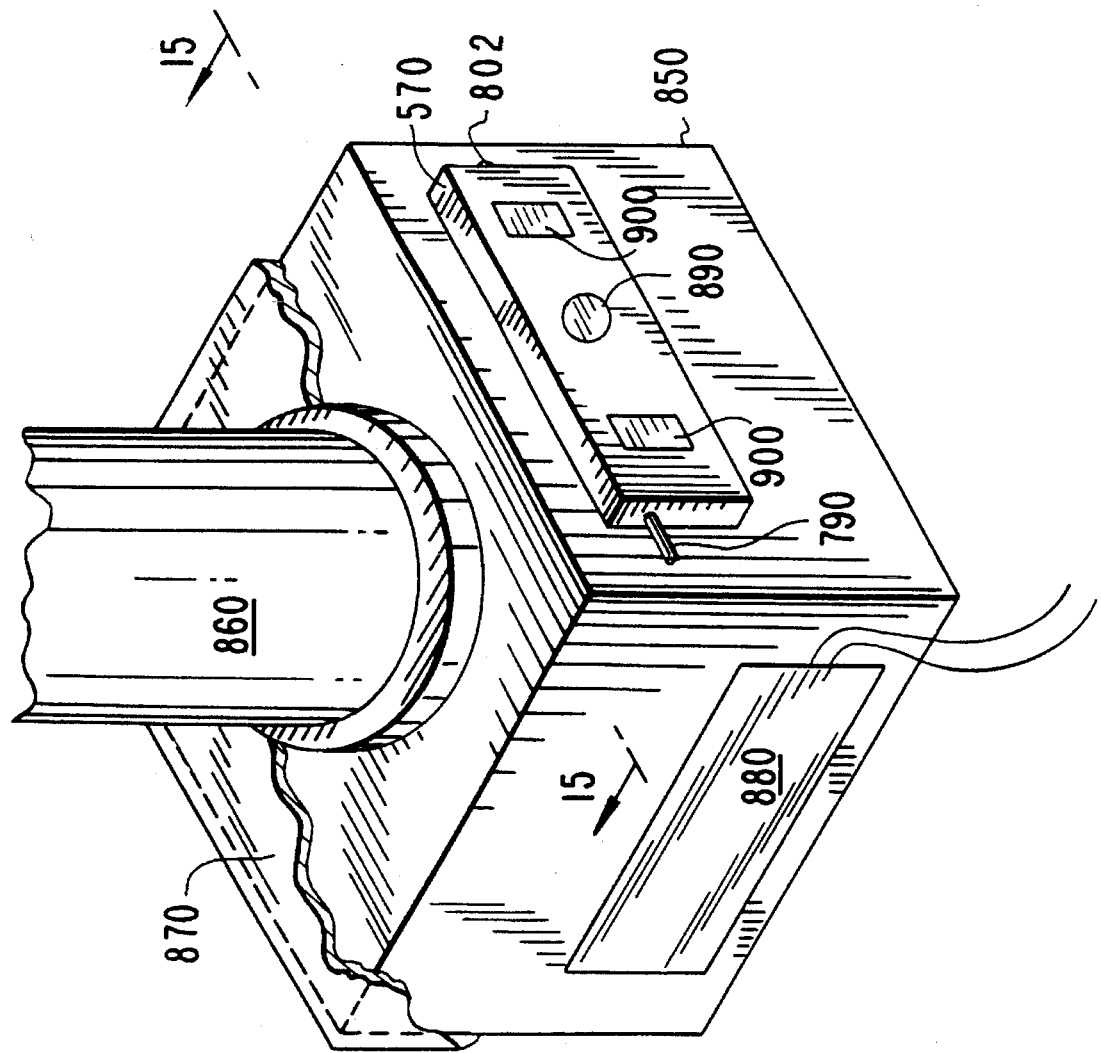
FIG. 12 is a partially broken away, perspective view of a flow cell housing and certain structurally related components of the FIG. 1 embodiment.

The flow cell 50 is mounted within an environmentally controlled housing 850, illustrated in FIG. 12. The housing 850 has a photomultiplier tube (PMT) 860 of the light detector system 60 mounted on an upper surface of the housing 850 and positioned to receive light produced through electrochemiluminescence in the flow cell 50 mounted beneath the PMT 860 within the housing 850. In order to reduce levels of background light which may interfere with the operation of the PMT 860, the housing 850 is sealed against stray light on all sides as well as at all openings, for example, where the PMT 860 is mated to the housing 850. The housing 850 is also insulated against heat conduction therethrough by an insulating cover 870 shown partially broken away for ease of illustration. The temperature within the housing 850 is controlled by means of the flow cell temperature control system 80 of FIG. 1 which serves to apply heat to the exterior of the housing 850 to maintain its interior temperature substantially at a predetermined value by means of foil heaters 880 adhesively affixed to three lateral sides of the housing 850 as well as to a bottom surface thereof. Further details of the flow cell temperature control system will be explained hereinbelow.

The heater block 570 is mounted on an exterior lateral surface of the housing 850 and is fabricated of a metal, such as brass, providing good heat conductivity. As shown in FIG. 12, the line 790 through which sample fluids, as well as cleaning fluids, assay buffers and air pass on their way to the flow cell 50 are conducted through the heater block 800 to adjust their temperatures to within at least a predetermined range of temperatures to permit the conduct of ECL tests on the sample fluids in a reproducible manner. As shown in FIG. 12, the fluids emitted from the heater block 570 are conveyed via the line 802 through the housing 850 and, as shown in FIG. 10, to the flow cell 50. A temperature sensor 890 is affixed to the heater block 800 to produce a signal representing the temperature thereof. In addition, two power transistors 900 are affixed to the heater block in order to controllably apply heat thereto for maintaining the temperature of the heater block at a desired level.

Figure 13:
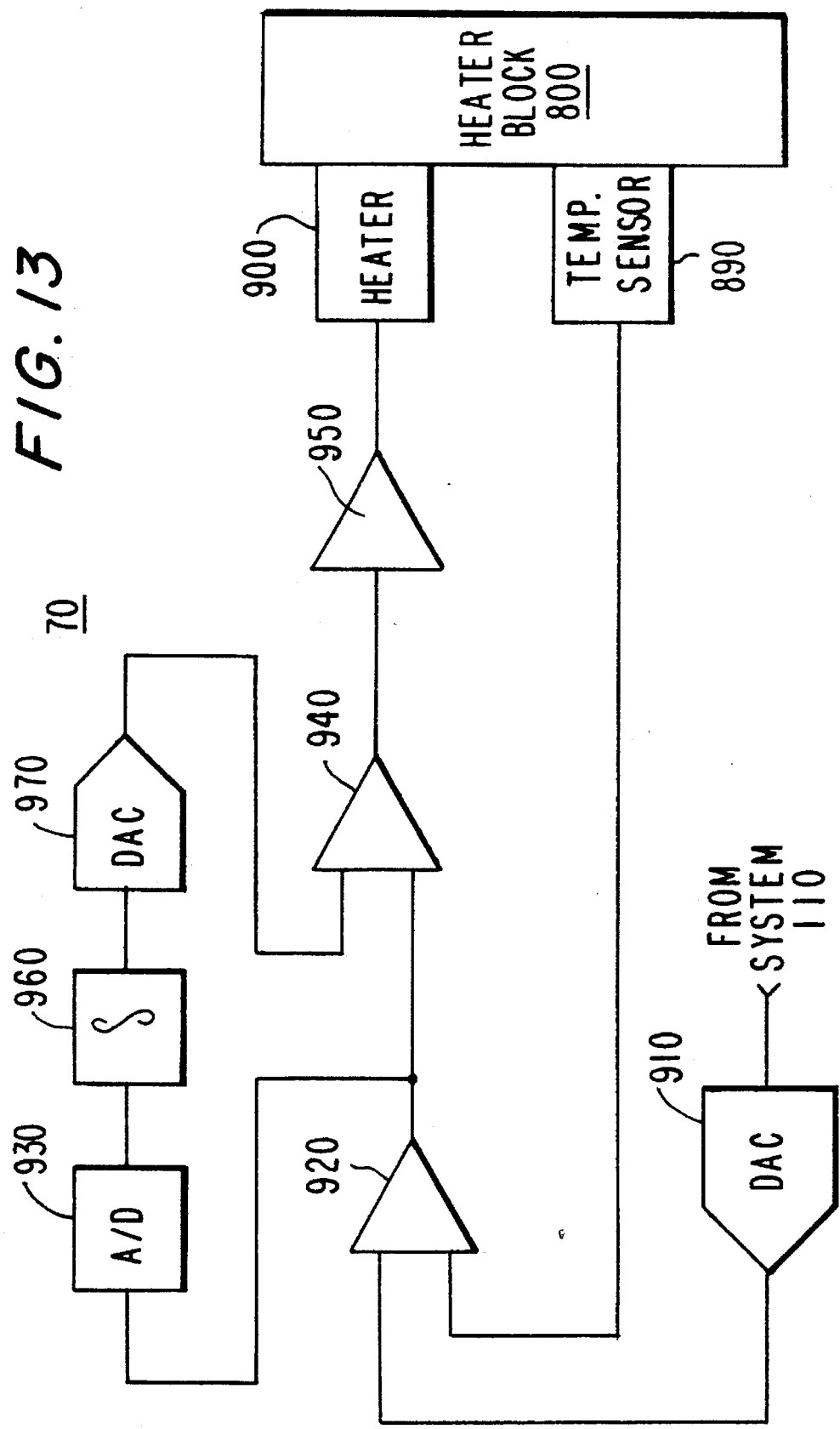
FIG. 13 is a block diagram of a sample fluid heater system of the FIG. 1 embodiment.

With reference now to FIG. 13, a functional block diagram of the sample fluid heater system 70 is illustrated therein. The sample fluid heater system 70 is implemented as a proportional/integral temperature controller in order to provide close correspondence between a desired temperature of the heater block 570 and the actual temperature thereof. A desired or set temperature of the heater block 570 is written to a DAC 910 by the control and signal/data processing system 110 so that the set temperature value in analog form is output by the DAC 910 to a first input of a difference amplifier 920. A second input of the difference amplifier 920 is provided with the output of the temperature sensor 890 and the difference amplifier 920 serves to produce an error voltage representing the difference between the set or desired temperature of the block 570 and the actual temperature thereof as sensed by the temperature sensor 890. The error voltage output by the difference amplifier 920 is supplied to the input of an analog-to-digital converter 930, as well as to a first input of a summing amplifier 940. An output of the summing amplifier 940 is supplied to the input of a driver 950 which serves to provide a controlled heating current to the power transistors 900 for controllably heating the block 800. The loop represented by the temperature sensor 890, difference amplifier 920, summing amplifier 940 and driver 950 represents a proportional controller loop, that is, a control loop in which the heating current is proportional to the difference between the set temperature and the measured temperature.

In the operation of a practical proportional control loop having a realistic gain (that is, a gain which is sufficiently limited to avoid instability and consequent oscillation), there typically is a steady state error between the measured value (here the actual temperature of the block 570) and the desired value (that is, the set temperature). Consequently, the system 70 also employs an integral controller loop which is implemented by the analog-to-digital converter 930, the control and signal/data processing system 110 acting as an integrator 960 as illustrated in FIG. 13, together with a digital-to-analog converter 970 which serves to convert the output of the integrator 960 to analog form and supply the same to a second input of the summing amplifier 940. In operation, the integral control loop, after each data acquisition from the analog-to-digital converter 930, adds the converted error voltage to an integral term which is stored by the system 110. This value is then scaled by an appropriate gain factor and written to the DAC 970 to be output in analog form to the second input of the summing amplifier 940. The output of the DAC 970 serves to substantially eliminate the steady state error associated with the proportional control loop. In certain instances, however, the integral value is modified to accommodate design limitations of the system. That is, when the error voltage is sufficiently large that the proportional control system alone will drive the power transistors at maximum power, the integral term is set by the system 110 to zero. In addition, if the integral term becomes sufficiently large that it likewise will drive the power transistors at full power, the amount of the integral is prevented from increasing so that it does not accumulate past a point where it can have any further effect on the temperature of the heater block 570.

Figure 14:
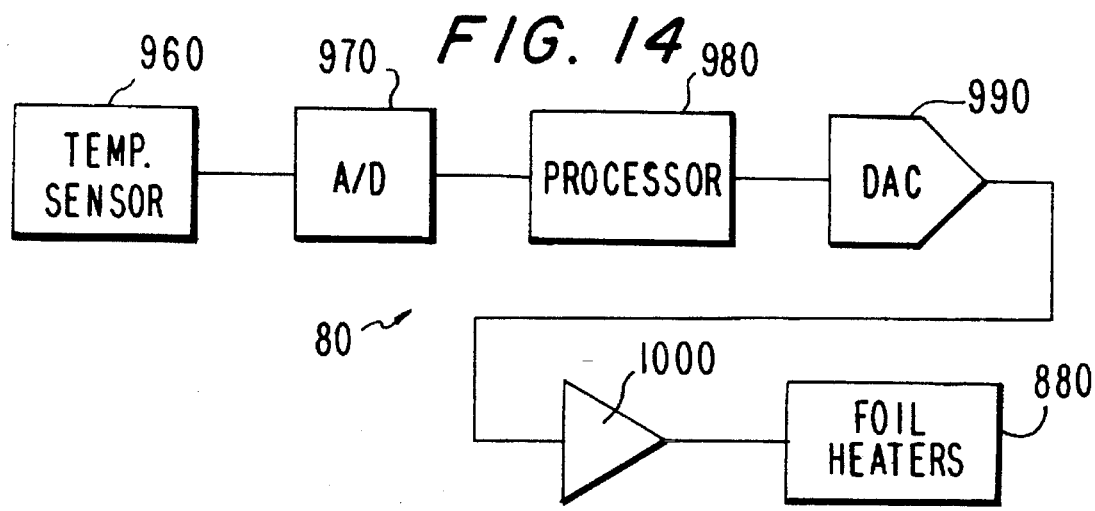
FIG. 14 is a block diagram of a temperature control system for the flow cell housing of FIG. 12.

With reference now to FIG. 14, a block diagram of the flow cell temperature control system 80 is illustrated therein. While the flow cell temperature control system 80 of FIG. 1 may be implemented in the manner illustrated in FIG. 13 for the sample fluid heater system 70, the system as illustrated in FIG. 14, is implemented entirely by the control and signal/data processing system 110. That is, the flow cell temperature control system 80 includes a temperature sensor 960 mounted on the flow cell 50 within the housing 850 and is coupled with an analog-to-digital converter 970 which digitizes the output of the temperature sensor 960 and provides the same to the system 110 acting as a control loop processor 980. The control loop processor 980 carries out both the proportional and integral processing functions as performed by the system 70 of FIG. 13 (described hereinabove) and outputs a digital value to the input of a digital-to-analog converter (DAC) 990 representing a drive current to be applied to the foil heaters 880 adhesively affixed to the exterior of the housing 850 of FIG. 12. The DAC 990 converts the drive value to analog form and supplies the same to the input of a driver 1000 which serves to apply a corresponding heating current to the foil heaters 880. As an alternative to the dual systems of FIGS. 13 and 14, in certain applications the system 80 of FIG. 14 can be eliminated and the foil heaters 880 driven instead by the driver 950 of the system 70 (FIG. 13). In addition, in place of heating elements, cooling elements may likewise be used to establish a predetermined test temperature. Such cooling elements include, for example thermoelectric coolers and Peltier coolers. A further alternative is to subject the apparatus to a temperature controlled medium, either liquid or gas (such as air).

Figure 15:
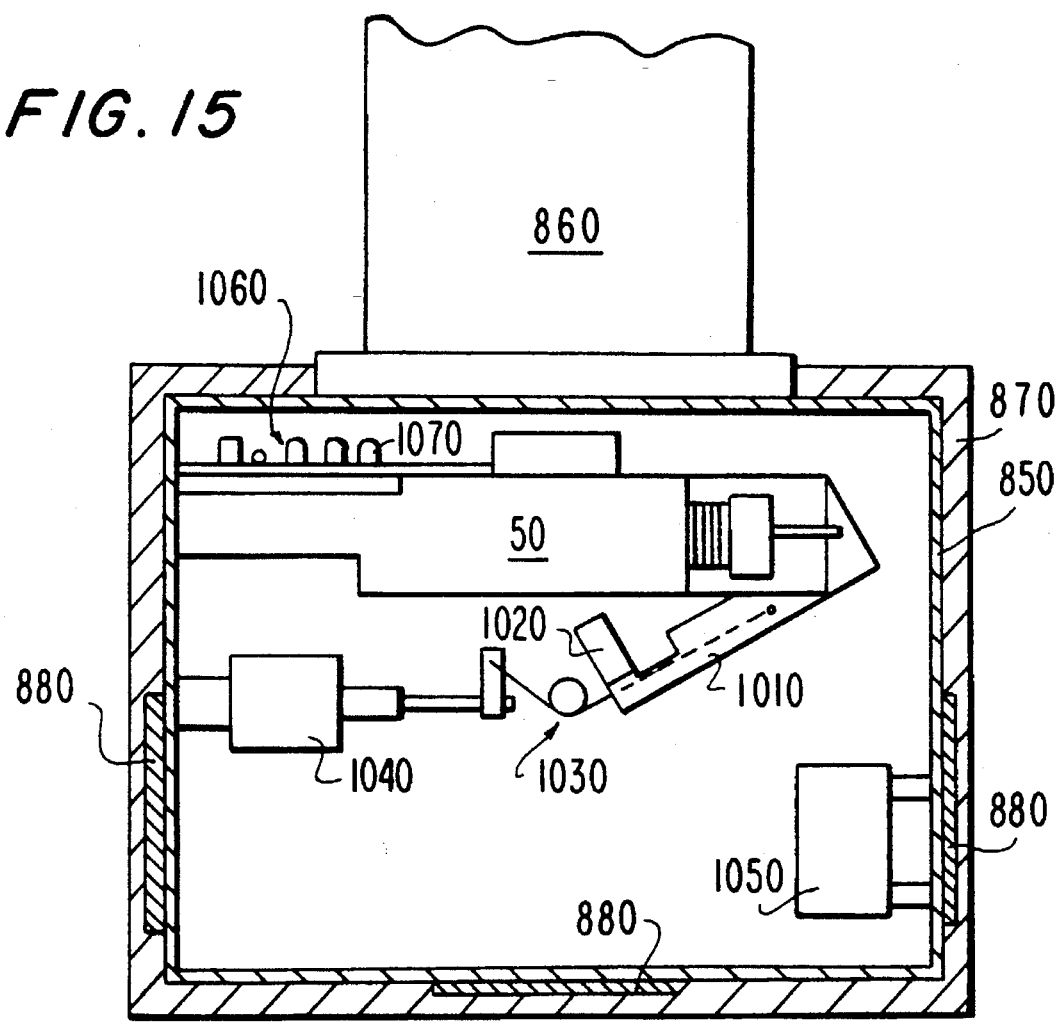
FIG. 15 is a cross-sectional view taken along the lines 15—15 in FIG. 12.

In the cross-sectional view of the interior of the housing 850 as shown in FIG. 15, the flow cell 50 is affixed to the housing 850 and spaced slightly below the upper surface thereof so that light emitted through electrochemiluminescence within the flow cell 50 propagates towards the PMT 860 to be converted thereby to an electrical signal representing an amount of light received thereby. The flow cell 50 includes an arm 1010 pivotally mounted thereto, the arm having a permanent magnet 1020 affixed thereto so that the magnet 1020 may be pivoted either to a position in the vicinity of a working electrode of the flow cell 50 for use in collecting magnetic particles with bound ECL labels pursuant to a magnetic particle assay, or away from the flow cell 50, for example, when electrochemiluminescence of the ECL labels is induced in order to avoid interference with the operation of the PMT 860. The arm 1020 is coupled through a coil spring 1030 with an arm of a solenoid operated linear actuator 1040. When the solenoid of the linear actuator 1040 is deenergized, its arm is drawn outwardly by the coil spring 1030 so that the arm 1010 pivots away from the vicinity of the working electrode, as shown in FIG. 15. When the solenoid of the linear actuator 1040 is energized, the arm thereof is drawn within the housing of the actuator 1040, thus exerting a force on the coil spring 1030 which, in turn, rotates the arm 1010 upwardly to bring the magnet 1020 into a position adjacent the working electrode of the flow cell 50.

As also shown in FIG. 15, a motor driven fan 1050 is mounted within the housing 850 and runs continuously to circulate air within the housing 850 to maintain a substantially uniform temperature throughout its interior. As also shown in FIG. 15, a circuit board 1060 is mounted on the flow cell 50. The circuit board 1060 includes circuitry for coupling the working electrode as well as counter electrodes and a reference electrode included in the flow cell 50 with the system 110 for the purpose of applying voltage and current to the counter and working electrodes and to measure such voltages and currents as well as a voltage level on the reference electrode. Circuit board 1060 also includes a reference LED 1070 which may be energized selectively to emit a controlled amount of light toward the PMT 860 to enable calibration thereof.

FLOW CELL

The flow cell is now described with reference to FIGS. 16–18. The flow cell 50 includes a main housing 1080 fabricated of a durable, transparent and chemically inert material which is easy to machine or injection mold to the configuration illustrated in FIGS. 16–18. Suitable materials for the housing 1080 include acrylic and polymethyl methacrylate. The main housing 1080 has a first lower surface 1090 (FIG. 17) through which a fluid inlet defined by a threaded coupling 1100 and contiguous conduit 1110 are formed in the main housing 1080. As seen in FIG. 17, the conduit 1110 extends from the threaded coupling 1100 to an upper surface 1120 of the main housing 1080.

A fluid outlet is also formed in the main housing 1080 and includes a threaded coupling 1130 extending upwardly from a second lower surface 1140 of the main housing 1080 to a further conduit 1150 which extends therefrom to the upper surface 1120. An ECL test chamber or container 1174 is formed between the upper surface 1120 of the main housing 1180 and a lower surface of a transparent block 1160 affixed above the upper surface 1120 and separated therefrom by a gasket 1170 which defines lateral walls of the chamber 1174. The gasket 1170 forms a fluid tight seal between the block 1160 and the main housing 1080, the block 1160 and gasket 1170 being held to the main housing 1180 by a plurality of fasteners 1180 (FIG. 16). The chamber 1174 thus defined by the main housing 1080, the block 1160 and the gasket 1170 communicates with the conduit 1110 adjacent a first lateral side of the chamber 1174 and with the conduit 1150 at a second lateral side of the chamber 1174 opposite the first lateral side. Accordingly, fluids introduced through the fluid inlet defined by the coupling 1100 and conduit 1110 flow through the chamber 1174 from right to left as viewed in FIG. 17 and are emitted therefrom through the fluid outlet formed by the conduit 1150 and threaded coupling 1130, so that the fluid inlet, the chamber and the fluid outlet define a fluid flow path through the flow cell 50.

Figure 17:
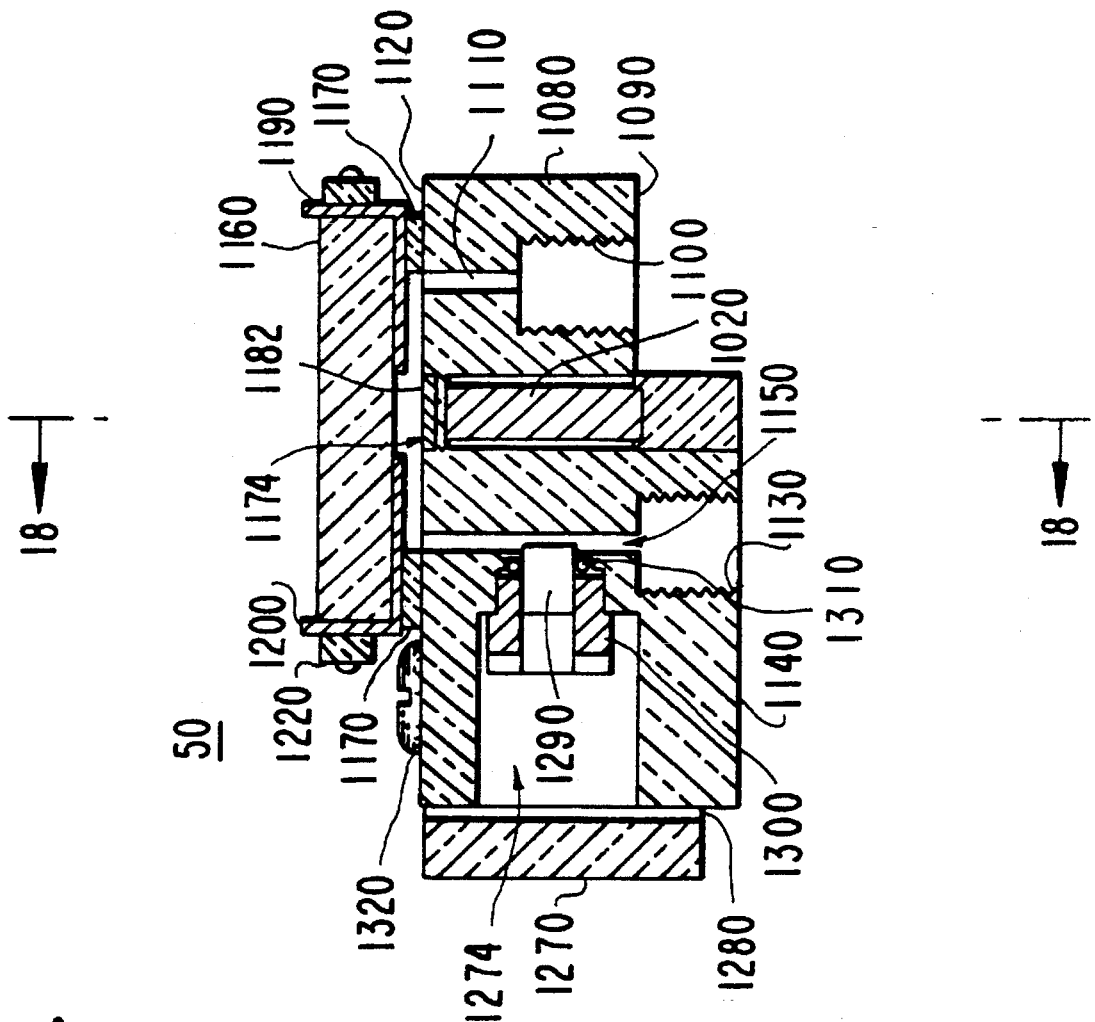
FIG. 17 is a cross-sectional view taken along the lines 17—17 in FIG. 16.
Figure 18:
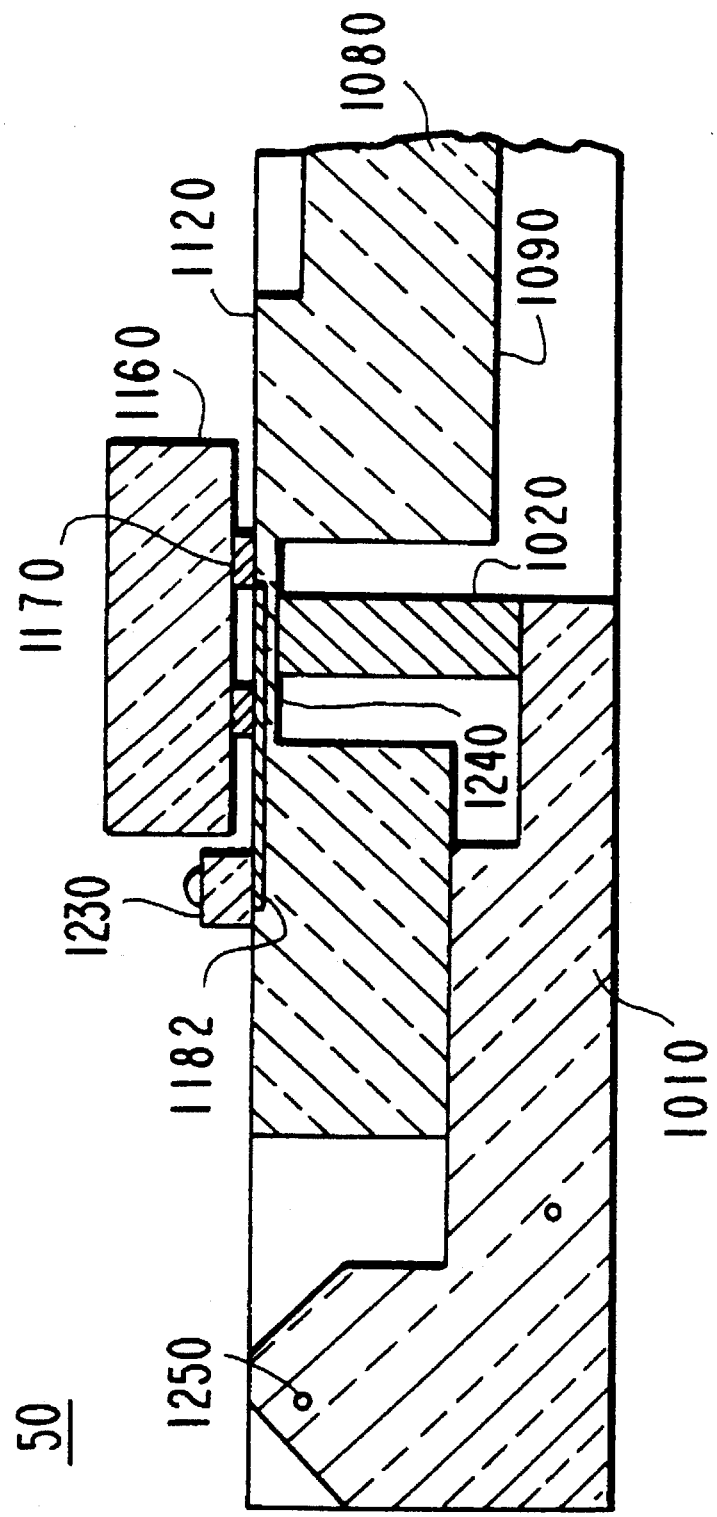
FIG. 18 is a cross-sectional view taken along the lines 18—18 in FIG. 17.

With reference in particular to FIGS. 17 and 18, a working electrode 1182 is arranged in a shallow groove formed in the upper surface 1120 of the main housing 1180 and has a longitudinal axis arranged generally transverse to a longitudinal axis of the chamber 1174 extending from the first lateral side thereof to its second lateral side and is positioned laterally centrally thereof between the conduits 1110 and 1150. The working electrode 1182 is held within the shallow groove in the top surface 1120 of the main housing 1080 by means of a first retainer block 1230 held against the surface 1120 by a pair of fasteners and serving to maintain a first electrical lead (not shown for purposes of simplicity and clarity) in conductive contact with the working electrode for coupling the same with the circuit board 1060.

Figure 16:
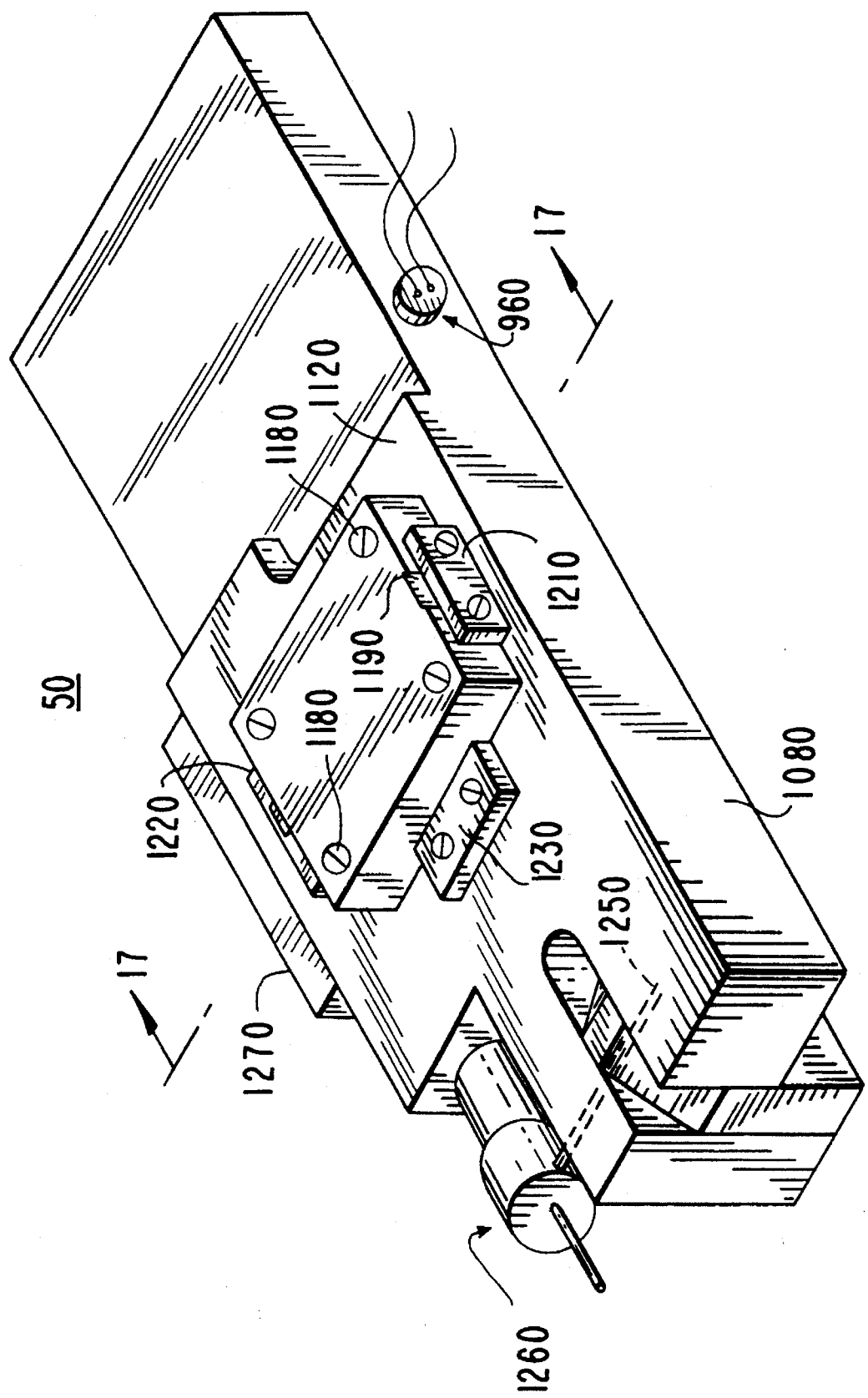
FIG. 16 is a perspective view of the flow cell of the FIG. 1 embodiment.

With reference particularly to FIGS. 16 and 17, a first counter electrode 1190 is arranged to extend along a bottom surface of the block 1160 forming an upper surface of the chamber 1174 from a position approximately opposite a first lateral side of the working electrode 1182 toward the first lateral side of the chamber 1174 adjacent the conduit 1110 and therebeyond between the gasket 1170 and the block 1160 and is forward upwardly at a right angle to extend along a first lateral side of the block 1160. The first counter electrode 1190 is held against the first lateral side of the block 1160 by a second retainer block 1210 fastened by a pair of fasteners to the block 1160 and which also serves to securely connect an electrical lead (not shown for purposes of simplicity and clarity) to the first counter electrode 1190 to couple the same with the circuit board 1060 (FIG. 15).

A second counter electrode 1200 extends along the bottom surface of the block 1160 from a position approximately opposite a second lateral side of the working electrode 1182 outwardly along the top wall of the chamber 1174 formed by the bottom wall of the block 1160 toward the conduit 1150 and therebeyond between the block 1160 and the gasket 1170 to a second lateral edge of the block 1160 where the second counter electrode is formed at a right angle to extend upwardly therealong. A third retainer block 1220 retains the second counter electrode against the second lateral side of the block 1160 by means of a further pair of fasteners and serves to securely couple a further electrical lead (not shown for purposes of simplicity and clarity) to the second counter electrode 1200 for coupling the same to the circuit board 1060. Materials suitable for the working electrode 1182 and the counter electrodes 1190 and 1200 include platinum and gold.

It will be seen especially from FIG. 17 that the counter electrodes 1190 and 1200 are arranged on a wall (that is, the bottom surface of the block 1160) of the chamber opposite a second wall thereof (that is, the upper surface 1120 of the main housing 1080) on which the working electrode 1182 is arranged. Conventional flow cells place the working and counter electrodes on the same wall of the chamber in which ECL is induced so that the emitted light can pass through an opposite transparent wall of the chamber to be detected by a PMT. However, certain electrode materials are prone to flake off as fluid flows by, thus tending to form a conductive bridge which shorts out the counter and working electrodes, thereby rendering the flow cell unusable until the conductive bridge has been removed by cleaning.

The flow cell 50 as shown particularly in FIG. 17 substantially alleviates this problem by positioning a counter electrode on a wall of the ECL chamber opposite a wall thereof on which the working electrode is arranged but positioned so that the surface of the working electrode does not oppose the counter electrode, but rather is arranged opposite a wall which is made of transparent material. Consequently, any material which may flake off either a counter electrode or the working electrode will not tend to form a conductive bridge between the counter and working electrodes, while at the same time light emitted by ECL labels adjacent the surface of the working electrode can be transmitted through the transparent wall to be detected.

A further advantage provided by the flow cell 50 of FIGS. 16–18 is provided by the arrangement of counter electrodes 1190 and 1200 on opposite sides of the working electrode 1182 which serves to minimize variations in the flow of electric current between the counter electrodes 1190 and 1200, on the one hand, and the working electrode 1182, on the other, which may be caused, for example, by variations in fluid flow or composition within the ECL chamber 1174.

As noted above in connection with FIG. 15, a magnet 1020 is mounted on an arm 1010 which is pivotally connected with the flow cell 50. With reference in particular to FIGS. 16 and 18, the arm 1010 and magnet 1020 are illustrated therein in an upper position in which the magnet 1020 is brought in close proximity to the working electrode, being separated therefrom only by a relatively narrow wall 1240 of the main housing 1080. In this upper position, the magnet 1020 serves to accumulate magnetic particles bound to ECL labels adjacent a surface of the working electrode exposed to fluids in the ECL chamber 1174 in carrying out magnetic particle assays. Since it is desirable to move the magnet 1020 downwardly away from the PMT 860 when ECL measurements are carried out, the arm 1010 is mounted to the main housing 1080 by a pivot pin 1250.

With reference in particular to FIGS. 16 and 17, a reference electrode 1260 includes, for example, a wire immersed in an ionic solution permanently retained by an outer glass housing capped at an outer end by a glass frit which permits ionic communication between the ionic fluid within the glass housing and fluids which may come in contact with the glass frit. Conventional flow cell structures bring the glass frit of the reference electrode directly in contact with fluids within the fluid flow path, so that ionic exchange takes place therewith and the chemical composition of the ionic fluid within the glass housing of the reference electrode gradually changes so that the electrical characteristics of the reference electrode change or drift disadvantageously over time.

The flow cell 50 of FIGS. 16–18 substantially alleviates this problem by interposing a further ionic fluid between the flow path and the ionic fluid within the reference electrode. Moreover, the second ionic fluid is retained within a chamber 1274 formed by the main housing 1080 and a lateral block 1270 held to the main housing by a plurality of fasteners and sealed thereagainst by a further gasket 1280. The block 1270 may be made, for example, of the same material as the main housing 1080. As shown in FIG. 16, the reference electrode 1260 is inserted into the chamber formed between the block 1270 and the main housing 1080 to bring its glass frit into contact with an ionic conductive medium therein. A glass or ceramic frit 1290 is positioned in an aperture within the main housing 1080 joining the conduit 1150 and the chamber 1274 and is retained therein by a plug 1300 which presses against an O-ring seal 1310 to seal the outer periphery of the frit 1290 against invasion of fluids from the conduit 1150 or loss of ionic conductive media within the chamber 1274 to the conduit 1150.

A refill aperture is formed in the upper surface 1120 of the main housing 1080 extending to the chamber 1274 and is sealed by a removable plug 1320 which permits an ionic media within the chamber 1274 to be replaced. A suitable ionic conductive medium for filling the chamber 1274 is a gel including sodium chloride and agarose having a concentration selected to render the gel solid at room temperature, but liquefiable at 80° C. so that the same may be poured into the chamber 1274 through the aperture in the upper surface 1120 of the main housing 1080. The gel also contains phenolphthalein providing an indicator to detect leaks across the frit 1290. In particular, the phenolphthalein turns the gel pink when cleaning fluid from the conduit 1150 comes in contact with the gel due to a change in pH of the gel brought about by the cleaning fluid.

As noted hereinabove, the temperature sensor 960 of the temperature control system of FIG. 14 is mounted on the flow cell 50 within the housing 850 of FIG. 15. As shown in FIG. 16, the temperature sensor 960 is mounted on a side wall of the main housing 1080.

CONTROL AND SIGNAL/DATA PROCESSING SYSTEM

Figure 19A:
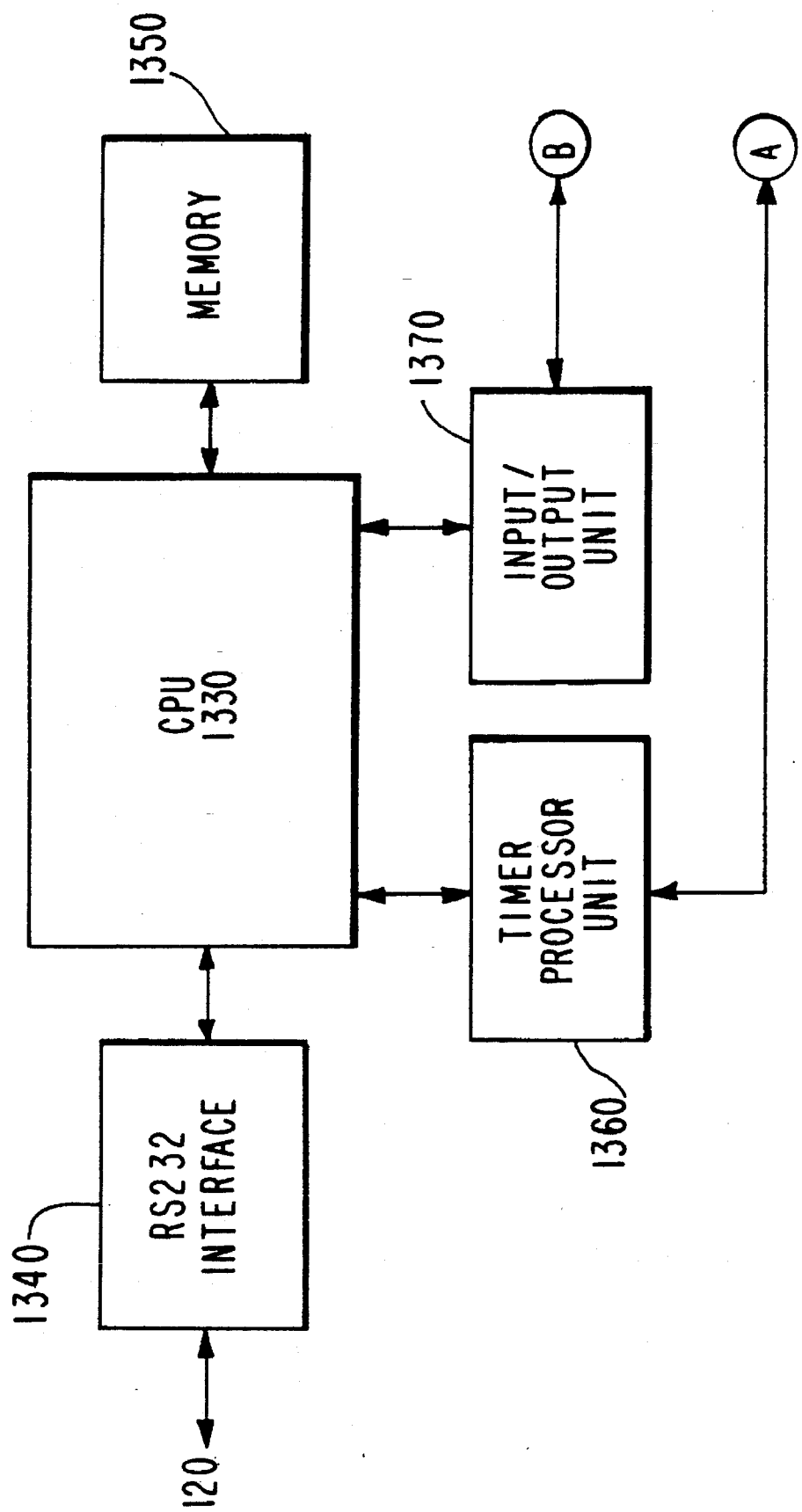
FIGS. 19A through 19C together provide a block diagram of a control and signal/data processing system of the FIG. 1 embodiment.
Figure 19B:
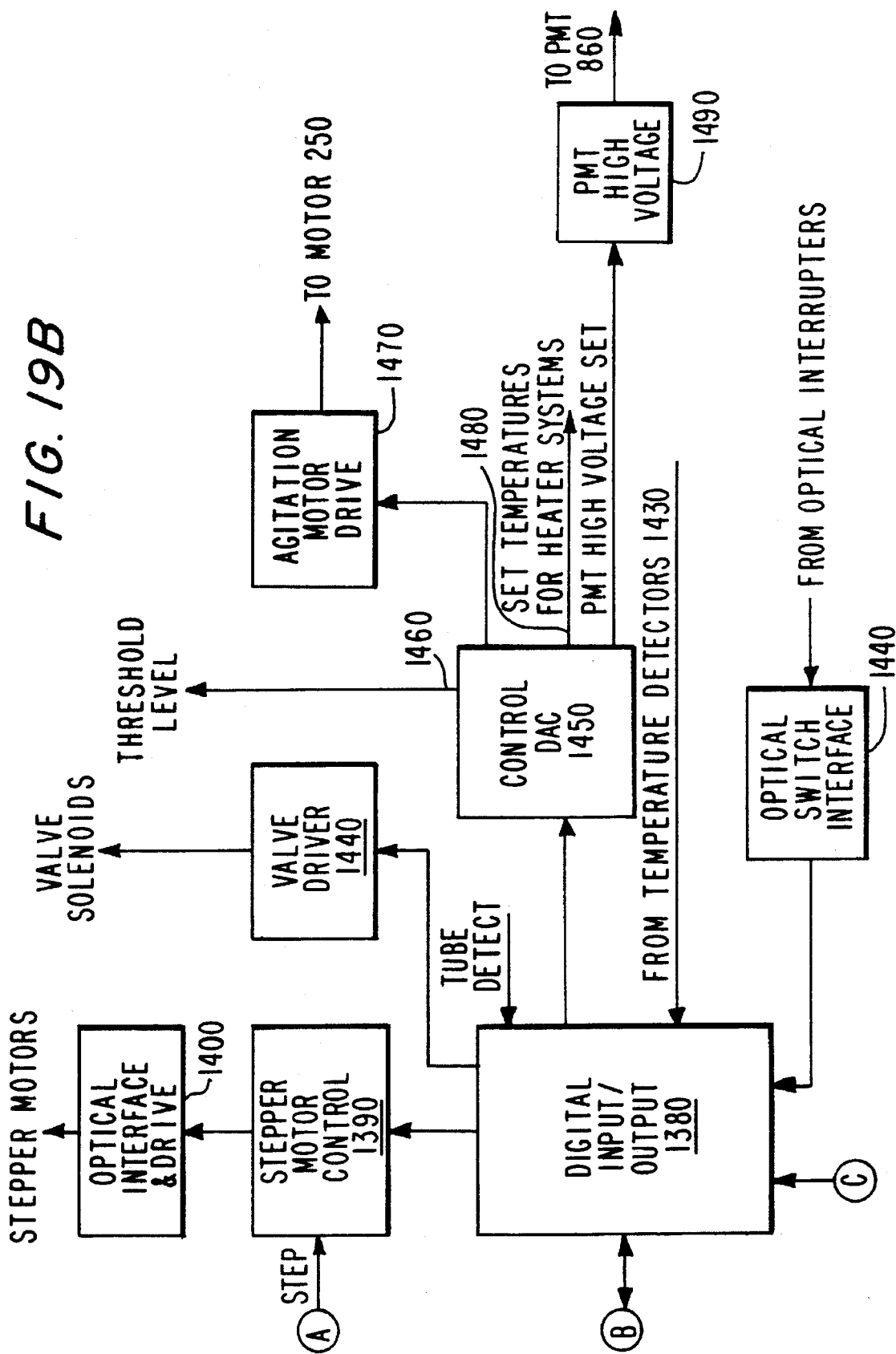
Figure 19C:
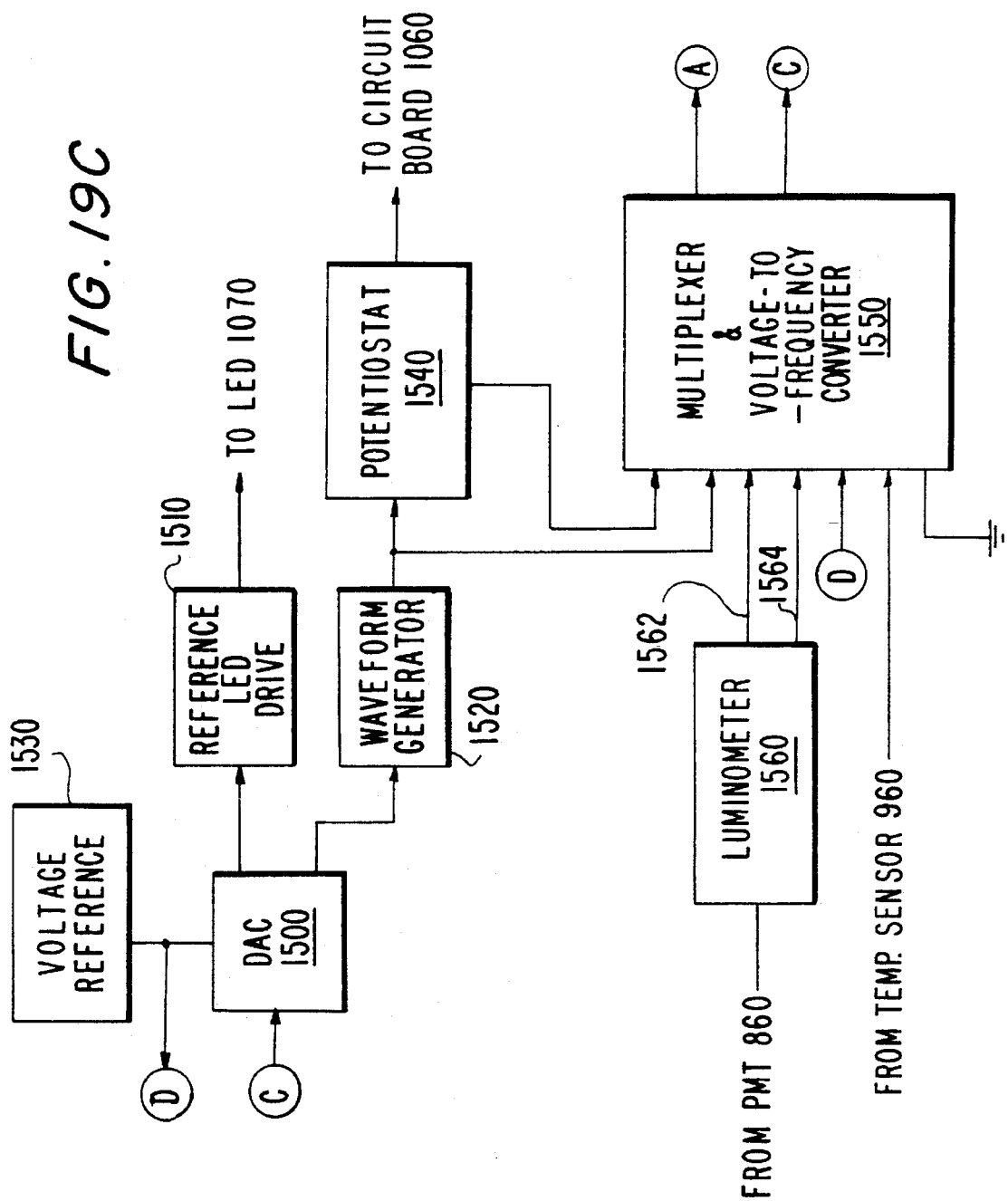

FIGS. 19A through 19C provide a block diagram of the control and signal/data processing system 110 of the FIG. 1 embodiment. With reference first to FIG. 19A, a central processing unit 1330 including a microprocessor, microcomputer or the like, is bidirectionally coupled with a RS 232 serial interface 1340 coupled with serial input/output port 120 for data communication. The CPU 1330 is also coupled bidirectionally with a memory 1350 including a RAM as well as nonvolatile storage, for example, provided by flash memory circuits. The CPU 1330 is operative to communicate with an external source of assay control programs through the interface 1340 to receive and store such programs in the memory 1350. The external programming source may be, for example, a personal computer in which a user inputs programs through a keyboard, disk drive, or other input device. As explained hereinbelow, the control and signal/data processing unit 110 is operative to receive and store a plurality of assay control programs, as well as to run such programs simultaneously to provide a multitasking capability which promotes efficient use of the apparatus. In addition, by permitting a user to create and run multiple programs, it is possible for the user to design and test relatively small portions of a more complex assay which greatly facilitates assay development.

The CPU 1330 is also bidirectionally coupled with a timer processor unit (TPU) 1360 in the form of a programmable timer device operative to generate and read clock signals. As explained in greater detail hereinbelow, the TPU 1360 is employed to generate stepper motor drive signals as well as to convert voltage-to-frequency converted values to a digital form which may be processed by the CPU 1330. The CPU 1330 is also bidirectionally coupled with an input/output unit 1370 which provides a digital communication capability between the CPU 1330 and various peripheral detection and drive circuits, as explained in greater detail below.

With reference also to FIG. 19B, the input/output unit 1370 is bidirectionally coupled with a digital input/output circuit 1380 which serves both as a digital multiplexer and dimultiplexer for digital signals provided from the input/output unit 1370 and various peripheral digital circuits, as well as for buffering various digital signals to be communicated to and from the peripheral circuits. As shown in FIG. 19B, the digital input/output unit 1380 is coupled with a stepper motor control circuit 1390, which is also coupled with the TPU 1360 to receive a stepper motor step pulse signal. The stepper motor control circuit 1390 serves to buffer direction and enable signals generated by the CPU 1330 and supplied via the digital input/output circuit 1380 for use in generating appropriate control signals to drive a selected one of the stepper motors of the apparatus selectably in high or low power mode and in normal or reverse direction. The stepper motor circuit 1390 includes separate latches to store direction and enable signals for each of the carousel rotating motor 390 (FIG. 6), the peristaltic pump 830 (FIG. 10), the linear actuator 1040 (FIG. 15) and the probe up/down drive motor described in connection with FIG. 11. The stepper motor control circuit is coupled with an optical interface and drive circuit 1400 to provide the various control signals for controlling the various stepper motors. The optical interface and drive circuit 1400 serves to decouple voltage spikes generated by the stepper motors from the remainder of the system 110 as well as to generate the necessary drive signals.

The circuit 1380 is also coupled with a valve driver circuit 1410 which serves to latch control signals for controlling the states of the solenoids in the manifold 620 as well as the state of the solenoid controlling the bypass valve 810, both as illustrated and described in connection with FIG. 10. The circuit 1410 likewise includes suitable driver circuits for driving the valve solenoids in accordance with the latched control signals. In particular, the manifold 620 includes three valves, each controlled by a respective solenoid for either communicating or blocking access from a respective inlet of the manifold 620 to the outlet line 650 thereof.

The circuit 1380 also receives the output of the D-type flip-flop 550 of the tube presence detection system of FIG. 9 and latches the same to be provided to the CPU 1330 for detecting the presence of a holder tube 142 at the pipetting position. The circuit 1380 has a plurality of inputs 1430 for receiving temperature detection signals from the various temperature control systems described hereinabove. In addition, the circuit 1380 has an input coupled with an optical switch interface circuit 1440 which, in turn, receives detection signals from the optical interrupter 472 of FIG. 9 (for detecting the homing position of the carousel 140), a home sensor for the probe 680 of FIG. 11, a home sensor for the pump 830 of FIG. 10 and a sensor providing a signal indicating whether the exterior housing 130 has been opened, in order to provide the system with the ability to shut down high voltage supplies in that event. The interface circuit 1440 conditions the detection signals from the various optical interruptors and latches the same for providing appropriate outputs to the circuit 1380 for provision to the CPU 1330 for control purposes.

The digital input/output circuit 1380 has a serial output coupled with a serial input of a control digital-to-analog converter 1450 which serves to latch digital values provided by the circuit 1380 and convert the same to analog form for carrying out various control functions described in greater detail hereinbelow. More particularly, the control DAC 1450 latches a threshold level signal for tube presence detection and converts the same to analog form which it supplies over an output 1460 to the comparator 540 of FIG. 9 (so that the control DAC 1450 implements the function of the DAC 560 as shown in FIG. 9). In addition, the control DAC 1450 latches a digital value representing a drive voltage for the agitation motor 250 and outputs the same in analog form to an agitation motor drive circuit 1470 which, in turn, provides a driving current to the motor 250. The control DAC 1450 also latches set temperatures for each of the temperature control systems 70 and 80 of FIG. 1 as well as the system 590 of FIG. 10 and outputs the same in analog form over a plurality of output lines indicated as 1480 in FIG. 19B. Finally, the control DAC 1450 latches a digital value received from circuit 1380 representing a high voltage level to be applied to the PMT 860 and converts the same to analog form which it supplies to a PMT high voltage power supply 1490 for controlling the high voltage applied thereby to the PMT 860.

Referring also to FIG. 19C, the digital input/output circuit 1380 outputs digital values representing reference LED drive level and waveform generation parameters to a digital-to-analog converter (DAC) 1500 having a plurality of addressable latches for storing these values to be supplied respectively to a reference LED drive circuit 1510 for supplying an appropriate drive level to the reference LED 1070 of FIG. 15 and to a waveform generator 1520 which serves to generate waveforms appropriate for driving the electrodes of the flow cell 50 for carrying out ECL measurements, as well as for cleaning and conditioning the electrodes. The DAC 1500 also receives a reference voltage level from a voltage reference circuit 1530.

In response to the analog values received from the DAC 1500, the waveform generator 1520 selectably generates either a ramp voltage waveform having a slope endpoint specified by the value supplied by the DAC 1500 or else a specified, constant output voltage. The waveforms thus produced by the waveform generator 1520 are supplied to an input of a potentiostat 1540. The potentiostat 1540 is coupled with each of the reference, counter and working electrodes and serves to apply the waveform received from the waveform generator 1520 so that the voltage level appearing at the reference electrode corresponds with the voltage output by the waveform generator 1520. Since the reference electrode does not conduct current, it will be seen with reference to FIG. 17 that the reference electrode will have a voltage level which is essentially the same as the voltage level on the counter electrode 1200. In addition, the counter electrode 1200 is coupled with the counter electrode 1190 on the circuit board 1060, so that the voltage level at the counter electrode 1190 is the same as that at the counter electrode 1200. Moreover, until current begins to flow between the counter electrodes and the working electrode 1182, the voltage level at the working electrode 1182 will be essentially the same as that on the counter electrodes and the reference electrode. However, once current begins to flow from the counter electrodes to the working electrode in response to a drive voltage applied between the counter and working electrodes by the potentiostat 1540, the voltage level at the surface of the working electrode falls below that of the counter and reference electrodes in proportion to the amount of current flowing between the counter and working electrodes. This provides the advantage of reducing the slope in the voltage waveform at the surface of the working electrode which leads to an improvement in measurement sensitivity. Further details of the operation of the waveform generator 1520 and the potentiostat 1540 may be obtained with reference to U.S. Pat. No. 5,068,088 issued Nov. 26, 1991 entitled Method and Apparatus for Conducting Electrochemiluminescent Measurements.

The potentiostat 1540 produces a current sensing voltage representing current flowing between the counter and working electrodes, as well as values representing electrode voltage levels and supplies these signal in analog form to a first input of a multiplexer and voltage-to-frequency converter 1550 having a plurality of inputs at which it receives respective analog voltages to be multiplexed and converted to signals in the frequency domain which, in turn, it supplies to the digital input/output circuit 1380 and timer processor unit 1360 for conversion to a form suitable for processing by the CPU 1330. The circuit 1550 also receives the output of the waveform generator 1520, the reference voltage from the circuit 1530 and a temperature detection signal from the temperature sensor 960 (FIG. 16) for multiplexing and conversion in the same manner as the signals received from the potentiostat 1540. A luminometer 1560 receives the output of the PMT 860 and provides both a low gain output on an output terminal 1562 and a high gain output on an output line 1564 each of which is coupled with a respective input of the multiplexer and voltage-to-frequency converter 1550. The provision of low and high gain outputs from the luminometer 1560 provides a wide dynamic range of operation for the apparatus. Finally, the circuit 1550 has an input coupled to receive a ground level reference input.

CONTROL AND SIGNAL/DATA PROCESSING SOFTWARE

Figure 20:
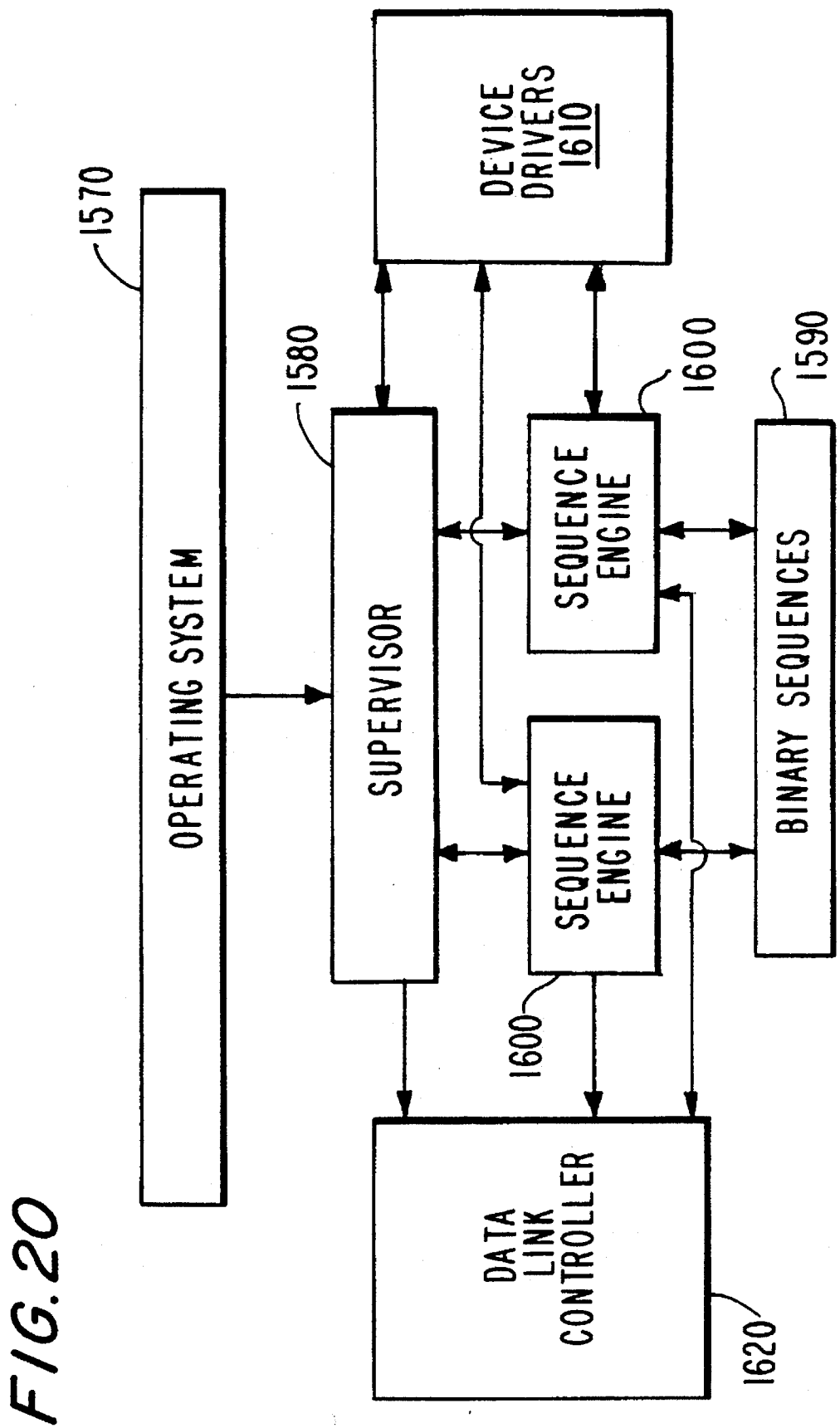
FIG. 20 is a functional block diagram of software used for controlling the operation of a central processor unit of the control and signal/data processing system of FIGS. 19A through 19C.

FIG. 20 provides a diagram illustrating the functional relationships among basic program elements of the software which controls the operation of the CPU 1330 of FIG. 19A. The system 110 employs a multitasking operating system 1570 on which a supervisor program 1580 runs for managing the overall operation of the system 110 and, therefore, the apparatus overall. The software also includes binary sequences 1590 each of which may be called by a higher level command to carry out a relatively specific, predefined task. Also included are a plurality of sequence engines 1600 each of which operates independently of the other sequence engines and acts as an interpreter for higher level commands, calling the binary sequences 1590 as appropriate to execute these commands. A number of device drivers 1610 execute commands which control instrument hardware, such as valves, stepper motors, and the like by outputting appropriate digital control signals via the input/output unit 1370 of FIG. 19A. The device drivers 1610 also control the storage of newly received assay control programs in non-volatile memory included within the memory block 1350 of FIG. 19A. Finally, a data link controller 1620 manages the data communications via the RS232 interface 1340, including activities such as packeting, routing and error checking.

The supervisor program serves to initialize the system, including setting up the device drivers 1610, initializing hardware and starting the data link controller task. In addition, the supervisor program starts a sequence engine 1600 in response to a command received by the serial input/output port 120 and then assumes a background status, awaiting an event requiring its intervention. Such events include, for example, a system error, a request for a system reset, and a failure of the data link, in which case some or all of the system may require initialization by the supervisor program. In addition, if the supervisor has initiated a plurality of sequence engines 1600 to run simultaneously, it serves to keep track of the system conditions overall and responds to any conflict between instructions carried out by different sequence engines in order to resolve the same.

The following Table I provides a summary of commands available to a user for programming the operation of the embodiment of FIG. 1, which may be entered via the serial input/output port 120 individually or in the form of an assay control program which is stored and selectably run by the control and signal/data processing system 110.

TABLE I

SUMMARY OF USER PROGRAMMABLE COMMANDS

| COMMAND | DESCRIPTION |
| --- | --- |
| Acquire | Start or stop capturing data representing either ECL luminosity (temperature compensated), dark current level, or reference level (LED reference 1070 on) |
| Carousel | Homes the carousel 140 or moves it to next tube position, as selected |
| Carpos | Moves the carousel 140 to a specified tube position |
| Cello | Turns off electrical supply to flow cell 50 by opening feedback loop of potentiostat 1540 and shorting its output |
| Heater | Sets a specified temperature for a selected one of the heating systems 70, 80 or 590 |
| Idel | Initiates a specified apparatus (instrument) delay |
| Ireset | Resets apparatus |
| Lumref | Turns on reference LED 1070 for calibration of PMT 860 |
| Magnet | Moves magnet 1020 up or down |
| PMT | Sets PMT 860 high voltage (to select PMT sensitivity according to requirements of selected assay) |
| Probe | Moves probe 680 up or down, as selected |
| Ptog | Changes the polarity of the waveform produced by the waveform generator 1520 and enables potentiostat 1540 |
| Pump | Homes peristaltic pump 830, turns the pump on at a specified speed and direction, or turns off the pump, as selected |

TABLE I-continued

SUMMARY OF USER PROGRAMMABLE COMMANDS

| COMMAND | DESCRIPTION |
| --- | --- |
| Ramp | Commands waveform generator 1520 to generate a ramp voltage waveform having a specified end point and slope, and enables potentiostat 1540 |
| Program Store | Stores assay control program received via RS232 interface |
| Valve | Turns a specified valve on or off, as selected |
| Volt | Commands waveform generator to output a constant, specified voltage level, and enables potentiostat 1540 |
| Vortex | Sets rotational speed of agitation motor 250 (from zero to a maximum value) |

Most of the commands summarized in Table I are followed by an argument providing further information necessary for carrying out the command, such as a device to be operated, a device state (speed, direction, on/off state, position) or signal to be generated. For example, the Acquire command requires an argument specifying the type of data to be captured while the Heater command requires an argument specifying the particular heating system 70, 80 or 590 for which the temperature is to be set. The Acquire command, as will be seen from Table I, also starts or stops a data capture activity, as specified by the argument. In addition, when Acquire is called to terminate the capture of ECL luminosity data, a temperature compensation task is carried out. More specifically, the memory 1350 stores a table of values which specify the amount of an adjustment which must be made in a given ECL luminosity reading depending on the deviation of the actual sample fluid temperature from a nominal testing temperature. In other words, the memory means stores data representing temperature dependence of light produced through electrochemiluminescence. In carrying out the temperature compensation routine, the temperature measured by the temperature sensor 960 mounted on flow cell 50 is employed to access the appropriate compensation data for this purpose.

EXEMPLARY ASSAY

Following is a description of an exemplary magnetic particle ECL assay for obtaining a number of ECL measurements for samples presented in respective holder tubes 142 mounted by a user in the carousel 140 (FIG. 4). It will be appreciated that, since the apparatus is programmable, further assays may be carried out thereby which differ substantially from the described exemplary assay, but which still employ the features of the present invention and, thus, are within the scope of the claims hereof.

Figure 21A:
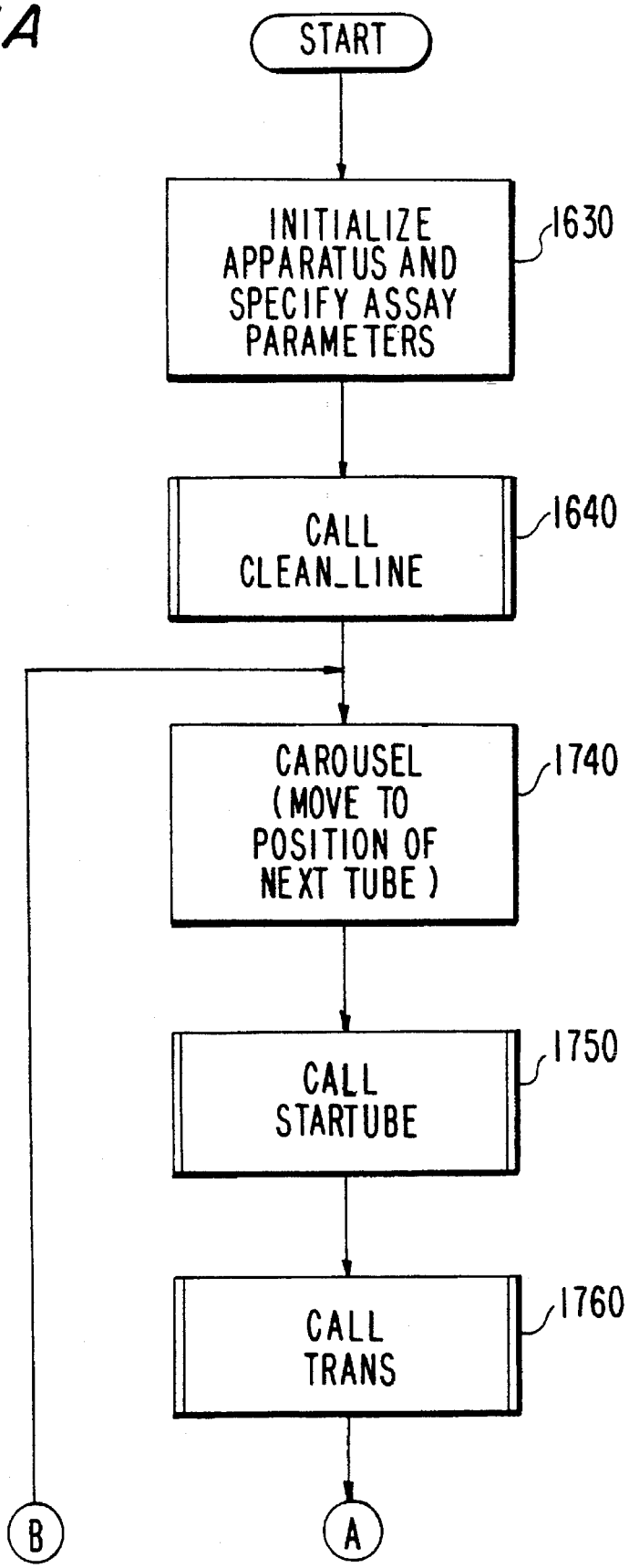
FIGS. 21A and 21B together provide a flow chart of a main processing loop of an exemplary assay control program input to the system of FIGS. 19A through 19C.
Figure 21B:
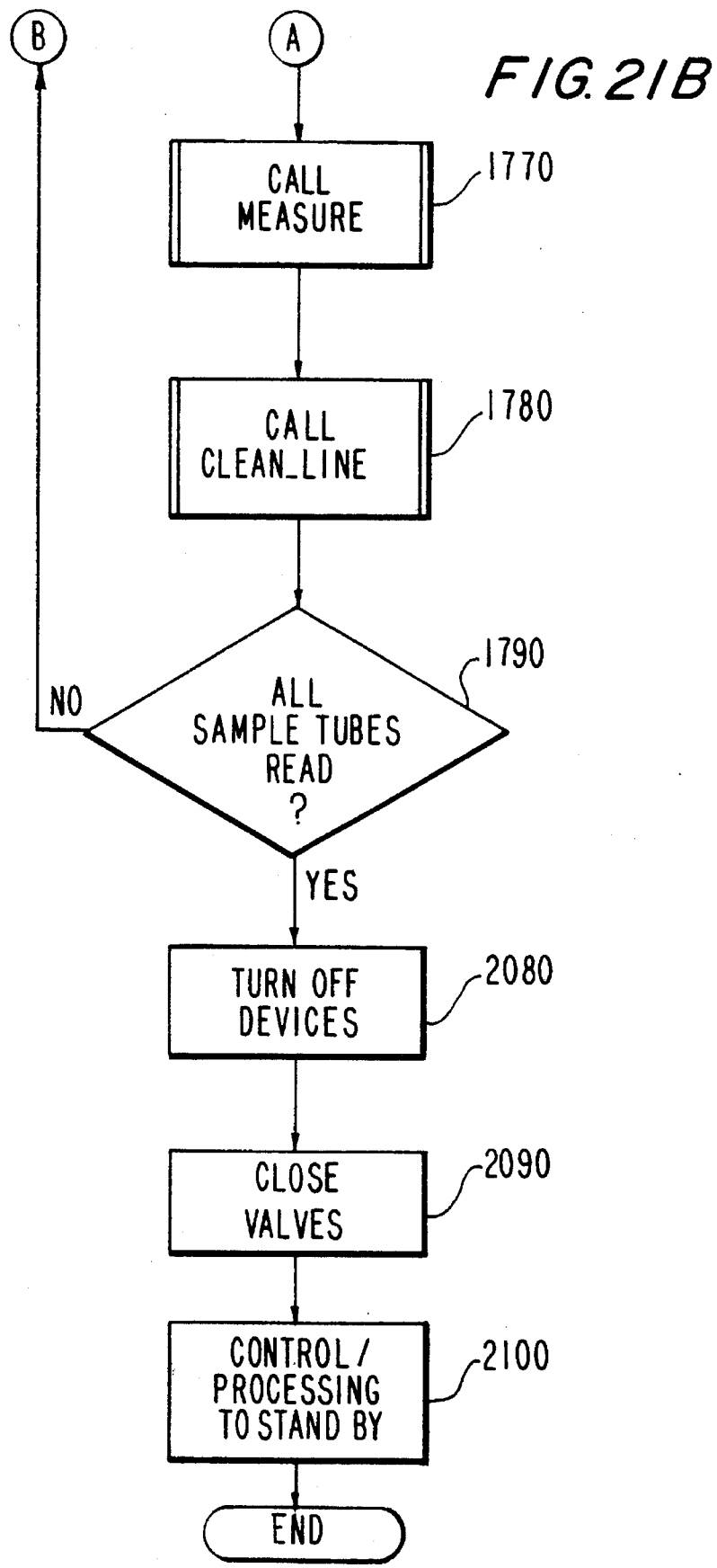
Figure 22A:
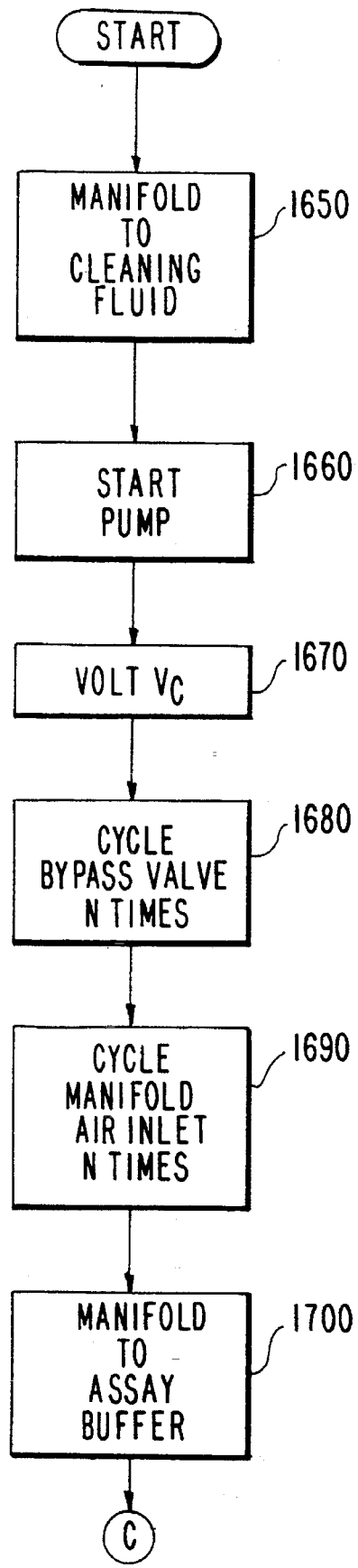
FIGS. 22A and 22B together provide a flow chart of a system cleaning sub-routine called by the main processing loop of FIGS. 21A and 21B.
Figure 22B:
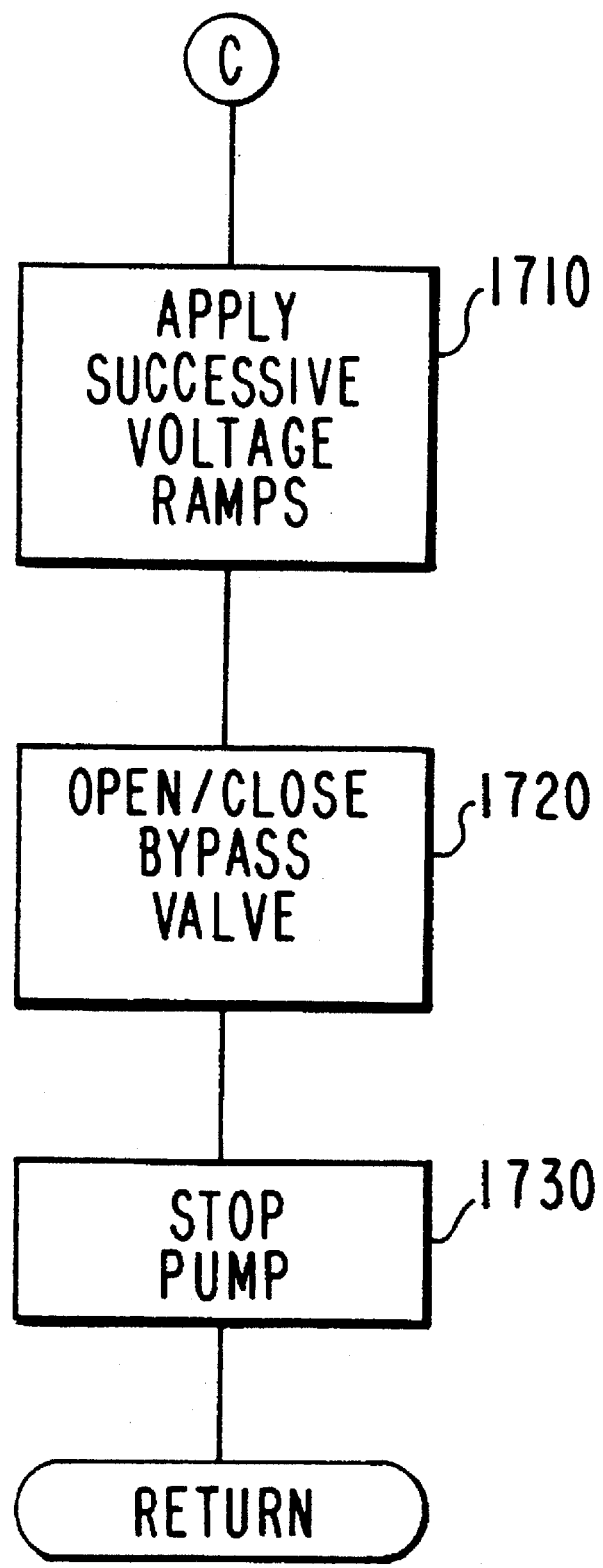

FIGS. 21A and 21B provide a flow chart of a main processing loop of the exemplary assay. With reference first to FIG. 21A, after processing has begun, the apparatus is initialized and assay parameters are specified, as indicated in step 1630. That is, the apparatus is reset by the Ireset command, followed by the specification of the parameters, the number of holder tubes 142 to be sampled in the course of the assay and the carrying out of a system cleaning subroutine Clean-line 1640. FIGS. 22A and 22B provide a flow chart of the Clean-line subroutine. When called, the Clean-line subroutine proceeds to actuate the cleaning fluid solenoid valve of the manifold to switch cleaning fluid to the outlet line 650 of the manifold 620, as indicated in step 1650 with the use of the Valve command summarized in Table I. In the following step 1660 the peristaltic pump is started by means of the Pump command and in a subsequent step 1670 a constant voltage level $V_c$ of the waveform generator is produced by means of the Volt command to set the voltage of the flow cell 50 substantially at the level $V_c$ in order to draw a cleaning fluid through the flow cell 50 at a predetermined cleaning voltage.

Thereafter in a step 1680, the bypass valve is turned on and off a predetermined number (N) of times by means of the Valve command in order to expel foreign material which may have become trapped in the T junction 780 (FIG. 10). Subsequently to the step 1680, in a step 1690, the manifold air inlet is turned on and off N times which serves to inject slugs of airs into the system (while the pump remains on) to mechanically dislodge particulate matter which is then carried away by the cleaning fluid. In the following step 1700, the assay buffer valve of the manifold is turned on (while the cleaning solution valve is turned off) to introduce assay buffer into the system. The clean line subroutine is concluded by stopping the pump in the step 1730.

Upon return to the main loop as illustrated in FIGS. 21A and 21B, the program begins executing a program loop including steps 1740 through 1790 repeatedly until all of the sample tubes have been read. In the repeated loop, the carousel is first moved to the position of the next tube by means of the Carousel command in step 1740. Thereafter a Startube subroutine 1750 is called.

With reference now to FIGS. 23A and 23B, the Startube subroutine serves to draw a sample fluid from a holder tube 142 at the pipetting position. Pursuant to the Startube subroutine, in a step 1800 the pump is brought to a home position in order to permit a precise amount of the sample to be withdrawn from the tube. In a subsequent step 1810 the vortexing motor is turned on by the Vortex command and thereafter the assay buffer valve of the manifold is opened by the Valve command in a step 1820. In the subsequent step 1830, the pump is turned on to draw the assay buffer through the flow cell while a succession of voltage ramps is applied in the step 1840 to condition the working electrode by bringing it into a reproducible electrochemical condition by either removing or forming an oxide layer at its working surface. Thereafter the voltage is maintained at a preset value in order to apply a predetermined constant potential to the working electrode, so that the working electrode is conditioned to ensure reproducible test results.

Thereafter, the vortexing motor is turned off (step 1850), the pump is turned off and returned to its home position (step 1860) and the assay buffer valve is closed (step 1870), in preparation to aspirate the sample from the holder tube. Once these steps have been accomplished, the probe 680 is lowered into the holder tube pursuant to the Probe command in step 1880, and the magnet is brought to its up position in a step 1890 pursuant to the Magnet command in order to attract magnetic particles with bound ECL labels to the surface of the working electrode when the sample fluid enters the flow cell 50. Then the sample is drawn into the probe in a succession of steps 1900, 1910 and 1920 pursuant to which the pump is turned on and maintained in the on state for a predetermined period of time determined by means of the Idel command in step 1910 at the end of which the pump is turned off in a step 1920. When the pump is turned off, a precisely measured amount of the sample has been drawn into the probe 680 which is then withdrawn from the sample tube by means of the Probe command, as indicated in a step 1930 and processing returns to the main processing loop of FIGS. 21A and 21B.

Figure 24:
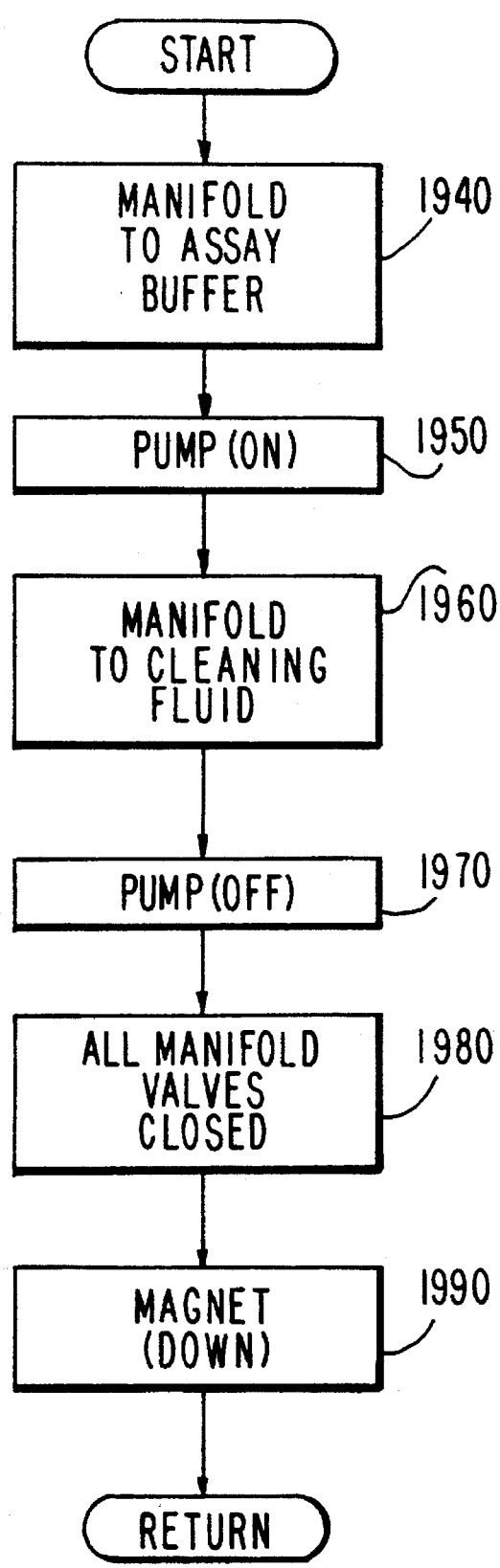
FIG. 24 is a flow chart of a flow cell fluid transfer sub-routine called by the main loop of FIGS. 21A and 21B.

Upon return to the main loop, the program calls a Trans subroutine in a step 1760 during which the sample fluid is drawn through the flow cell 50 at a controlled rate for the purpose of accumulating the magnetic particles in the fluid adjacent the working electrode in a controlled manner to ensure reproducibility of the test results. Pursuant to the Trans subroutine, as illustrated in FIG. 24, the assay buffer valve of the manifold is turned on to supply assay buffer to the outlet line 650 thereof in a step 1940. In a subsequent step 1950 the pump is turned on to draw assay buffer into the system for a predetermined period of time and at a controlled rate so that the sample fluid which precedes the assay buffer in the fluid transfer system is controllably drawn through the flow cell 50, as mentioned above, followed by assay buffer to remove sample particles which have not been captured by the magnet at the surface of the working electrode. Thereafter in a step 1960 the cleaning fluid valve of the manifold is turned on (and the assay buffer valve turned off) for a predetermined period of time to introduce cleaning fluid into the system, although not yet into the flow cell 50. At the end of the predetermined period of time, the pump is turned off in a step 1970, all of the manifold valves are closed (step 1980) and the magnet is moved to the down position (step 1990) in preparation for carrying out the ECL measurement, whereupon the program returns once again to the main loop.

Figure 25:
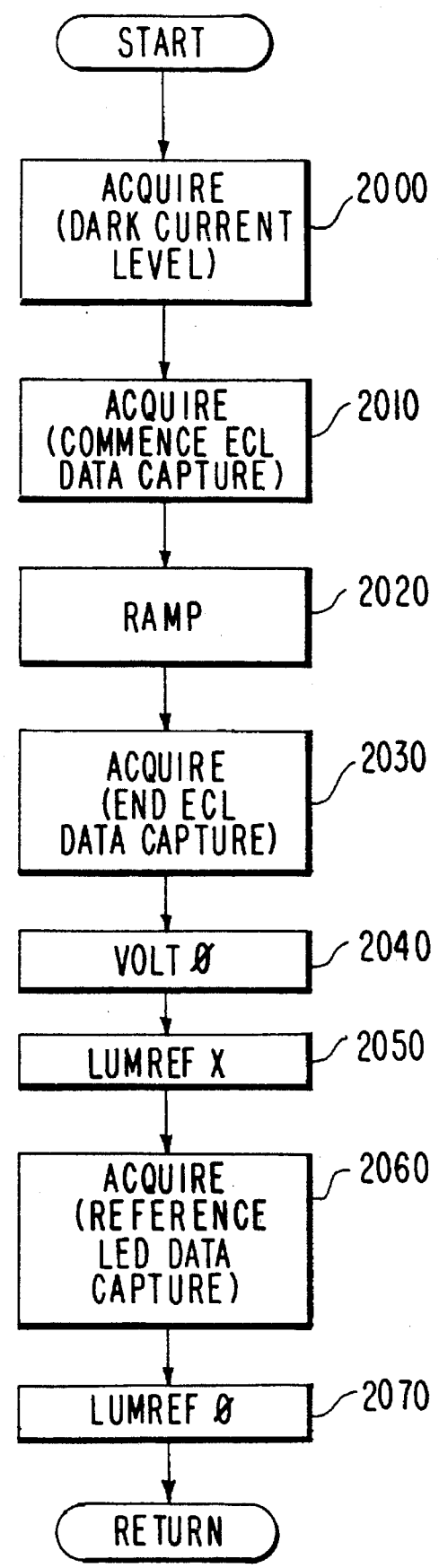
FIG. 25 is a flow chart of an ECL measurement sub-routine called by the main loop of FIGS. 21A and 21B.

Upon return to the main loop, a Measure subroutine (step 1770) is called for carrying out the ECL measurement. With reference to FIG. 25 in which the Measure subroutine is summarized, a dark current level of the PMT 860 is first obtained in a step 2000 (which actually represents three commands, namely, Acquire dark current level on, followed by Idel for a predetermined time period, and then Acquire dark current level off). Subsequently, a further Acquire command is executed to commence ECL data capture in a step 2010, whereupon a suitable sequence of ramp voltage waveforms are applied to the flow cell 50, as indicated in a step 2020, in order to controllably induce electrochemiluminescence by the sample fluid in the flow cell 50. After a predetermined period of time, the Acquire command is again executed to end ECL data capture, as indicated in step 2030. Once the ECL data capture task has been completed, the flow cell voltage is set at zero (step 2040), an excitation voltage is applied to the reference LED by executing the Lumref command (step 2050) and an Acquire sequence (step 2060) is carried out to capture PMT readings to provide a reference for evaluating the operating state of the PMT. Once the reference data has been captured, the reference LED is turned off (step 2070) and the program returns once again to the main loop. Following the Measure subroutine, the Clean-line subroutine (step 1780) is again carried out and, in the subsequent step 1790, it is determined whether all of the sample tubes have been read. If not, the program returns to the step 1740 to begin a further measurement sequence to measure the sample contents of the next holder tube.

Once all of the measurements have been carried out pursuant to the exemplary assay, the program in step 1790 proceeds to a step 2080 in which the various apparatus devices are turned off, followed by a step 2090 in which the various valves of the apparatus are closed, after which the control and signal/data processing system 110 is brought to a stand-by condition in step 2100 to complete the assay.

It will be appreciated that various elements of the present invention may be implemented in whole or in part using either analog or digital circuitry and that all or part of the control functions as well as the signal and data processing functions thereof may be carried out either by hardwired circuits or with the use of a microprocessor, microcomputer or the like.

Although specific embodiments of the invention have been described in detail herein with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An apparatus for use in carrying out electrochemiluminescence test measurements, comprising:

a cell for containing an electrochemiluminescent sample fluid;

a working electrode having an electrode surface within the cell;

a supply of electrical energy coupled with the working electrode for supplying electrical energy to the electrochemiluminescent sample fluid within the cell;

output signal producing means for producing an output signal representing a detected value based on light produced through electrochemiluminescence of the sample fluid within the cell; and temperature effect adjustment means for carrying out at least one of adjusting a temperature of the electrochemiluminescent sample fluid to a value at least within a predetermined range of temperature values, and adjusting the output signal based on the temperature of the electrochemiluminescent sample fluid to produce a temperature effect adjusted output signal.

2. The apparatus of claim 1, wherein the cell comprises a flow cell having a fluid inlet to receive the electrochemiluminescent sample fluid and a fluid outlet to conduct the electrochemiluminescent sample fluid from the flow cell; and further comprising a fluid transport system coupled with the fluid inlet and the fluid outlet for conducting the sample fluid to the fluid inlet and conducting the sample fluid from the fluid outlet.

3. The apparatus of claim 1, wherein the temperature effect adjustment means is operative to adjust the temperature of the sample fluid to a value within a predetermined range of temperature values.

4. The apparatus of claim 3, wherein the temperature effect adjustment means is operative to establish a predetermined temperature of the sample fluid within the predetermined range of temperature values.

5. The apparatus of claim 3, wherein the temperature effect adjustment means is operative to heat the sample fluid to a value within the predetermined range of temperature values.

6. The apparatus of claim 3, wherein the temperature effect adjustment means is operative to cool the sample fluid to a value within the predetermined range of temperature values.

7. The apparatus of claim 2 wherein the temperature effect adjustment means is operative to adjust the temperature of the sample fluid to a value within a predetermined range of temperature values as the sample fluid is conducted to the flow cell by the fluid transport system.

8. The apparatus of claim 3, wherein the temperature effect adjustment means comprises means for establishing a temperature of the cell within the predetermined range of temperature values.

9. The apparatus of claim 1, wherein the temperature effect adjustment means is operative to adjust the output signal based on the temperature of the electrochemiluminescent sample fluid to produce a temperature effect adjusted output signal.

10. The apparatus of claim 9, wherein the temperature effect adjustment means comprises memory means storing data representing temperature dependence of light produced through electrochemiluminescence, and means for adjusting the output signal based on the stored data.

* * * * *